(12) United States Patent
Haines

(10) Patent No.: US 8,114,083 B2
(45) Date of Patent: Feb. 14, 2012

(54) METHODS AND APPARATUS FOR IMPROVED DRILLING AND MILLING TOOLS FOR RESECTION

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 591 days.

(21) Appl. No.: 11/075,552

(22) Filed: Mar. 8, 2005

(65) Prior Publication Data

US 2006/0015116 A1    Jan. 19, 2006

Related U.S. Application Data

(63) Continuation-in-part of application No. 11/036,584, filed on Jan. 14, 2005, and a continuation-in-part of application No. 11/049,634, filed on Feb. 2, 2005.

(60) Provisional application No. 60/551,262, filed on Mar. 8, 2004, provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,631, filed on Mar. 8, 2004, provisional application No. 60/551,307, filed on Mar. 8, 2004, provisional application No. 60/551,160, filed on Mar. 8, 2004, provisional application No. 60/536,320, filed on Jan. 14, 2004, provisional application No. 60/540,992, filed on Feb. 2, 2004.

(51) Int. Cl.
*A61B 17/00* (2006.01)

(52) U.S. Cl. ............................ 606/79; 606/86 R; 606/88

(58) Field of Classification Search .............. 606/79–81, 606/60, 62–68, 329, 86 R, 88, 89, 96, 97, 606/98, 103, 104, 228, 232; 623/13.11–13.19
See application file for complete search history.

(56) References Cited

U.S. PATENT DOCUMENTS 2,697,433 A    12/1954 Zehnder
(Continued)

FOREIGN PATENT DOCUMENTS

EP    0104732    4/1984
(Continued)

OTHER PUBLICATIONS

T.D.V. Cooke et al., *Universal Bone Cutting Device for Precision Knee Replacement Arthroplasty and Osteotomy*, 7 J. Biomed. Eng'g 45, 47, col. 2, ll. 52-57 (1985).

(Continued)

*Primary Examiner* — Eduardo C Robert
*Assistant Examiner* — Tara Carter
(74) *Attorney, Agent, or Firm* — Patterson Thuente Christensen Pedersen, P.A.

(57) ABSTRACT

Milling and drilling tools and soft tissue management techniques are provided for arthroplasty that facilitate intraoperative and postoperative efficacy and ease of use. In one embodiment, resiliently biased soft tissue protective sleeves surround a side cutting tool and are interposed along the longitudinal axis of the cutting tool, preferably adjacent each side of the bone. The soft tissue protective sleeves are biased to track along the contour of the side of the bone and prevent the cutting tool from being exposed to soft tissue during the resection. In another embodiment, a pilot drill is initially utilized to create an initial bore in the bone to be resected. The pilot drill preferably has an end cutting arrangement and a non-cutting removal channel that minimizes the tendency of the pilot drill bit to drift off-axis as the initial bore in the bone is created. Once the initial bore is created, the pilot drill bit is withdrawn and a second side cutting tool, such as a milling bit, is then inserted into the bore to perform the desired surface resection.

19 Claims, 35 Drawing Sheets

U.S. PATENT DOCUMENTS

| | | |
|---|---|---|
| 3,457,922 A | 7/1969 | Ray |
| 3,739,662 A | 6/1973 | Windelman et al. |
| 3,748,662 A | 7/1973 | Helfet |
| 3,774,244 A | 11/1973 | Walker |
| 3,798,679 A | 3/1974 | Ewald |
| 3,816,855 A | 6/1974 | Salch |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,000,525 A | 1/1977 | Klawitter |
| 4,016,606 A | 4/1977 | Murray |
| 4,069,824 A | 1/1978 | Weinstock |
| 4,178,641 A | 12/1979 | Gruendel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Peterson |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,808,185 A | 2/1989 | Penenberg |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,963,153 A | 10/1990 | Noesberger |
| 4,971,075 A | 11/1990 | Lee |
| 4,979,949 A | 12/1990 | Matsen |
| 4,986,833 A | 1/1991 | Worland |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Warsaw |
| 5,098,436 A | 3/1992 | Ferrante |
| 5,100,409 A | 3/1992 | Coates |
| 5,108,398 A | 4/1992 | McQueen |
| 5,112,336 A | 5/1992 | Krevolin |
| 5,116,375 A | 5/1992 | Hofmann |
| 5,122,144 A | 6/1992 | Bert |
| 5,129,909 A | 7/1992 | Sutherland |
| 5,133,758 A | 7/1992 | Hollister |
| 5,133,759 A | 7/1992 | Turner |
| 5,137,536 A | 8/1992 | Koshino |
| 5,147,364 A | 9/1992 | Comparetto |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Peterson |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferreante |
| 5,364,402 A | 11/1994 | Mumme |
| 5,370,699 A | 12/1994 | Hood |
| 5,370,701 A | 12/1994 | Fin |
| 5,391,170 A | 2/1995 | McGuire |
| 5,397,330 A | 3/1995 | Mikhail |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |

| | | | | | | |
|---|---|---|---|---|---|---|
| 5,514,139 | A | 5/1996 | Goldstein | 6,171,340 B1 | 1/2001 | McDowell |
| 5,514,143 | A | 5/1996 | Bonutti | 6,195,577 B1 | 2/2001 | Truwit |
| 5,520,694 | A | 5/1996 | Dance | 6,197,064 B1 | 3/2001 | Haines |
| 5,520,695 | A | 5/1996 | Luckman | 6,203,576 B1 | 3/2001 | Afriat |
| 5,540,695 | A | 7/1996 | Levy | 6,206,926 B1 | 3/2001 | Pappas |
| 5,542,947 | A | 8/1996 | Treacy | 6,210,443 B1 | 4/2001 | Marceaux |
| 5,549,683 | A | 8/1996 | Bonutti | 6,235,060 B1 | 5/2001 | Meesenburg |
| 5,549,684 | A | 8/1996 | Amino | 6,236,875 B1 | 5/2001 | Becholz |
| 5,549,688 | A | 8/1996 | Ries | 6,264,697 B1 | 7/2001 | Walker |
| 5,551,429 | A | 9/1996 | Fitzpatrick | 6,285,902 B1 | 9/2001 | Kienzle |
| 5,562,674 | A | 10/1996 | Stalcup | 6,306,146 B1 | 10/2001 | Dinkler |
| 5,569,262 | A | 10/1996 | Carney | 6,306,172 B1 | 10/2001 | O'Neil et al. |
| 5,571,100 | A | 11/1996 | Goble | 6,325,828 B1 | 12/2001 | Dennis |
| 5,578,039 | A | 11/1996 | Vendrely | 6,340,363 B1 | 1/2002 | Bolger |
| 5,593,411 | A | 1/1997 | Stalcup | 6,342,075 B1 | 1/2002 | MacArthur |
| 5,597,379 | A | 1/1997 | Haines | 6,348,058 B1 | 2/2002 | Melkent |
| 5,601,563 | A | 2/1997 | Burke | 6,361,564 B1 | 3/2002 | Marceaux |
| 5,601,566 | A | 2/1997 | Dance | 6,368,353 B1 | 4/2002 | Arcand |
| 5,609,645 | A | 3/1997 | Vinciguerra | 6,375,658 B1 | 4/2002 | Hangody |
| 5,611,802 | A | 3/1997 | Samuelson | 6,379,388 B1 | 4/2002 | Ensign |
| 5,613,969 | A | 3/1997 | Jenkins, Jr. | 6,401,346 B1 | 6/2002 | Roberts |
| 5,628,749 | A | 5/1997 | Vendrely | 6,406,497 B2 | 6/2002 | Takei |
| 5,639,279 | A | 6/1997 | Burkinshaw | 6,413,279 B1 | 7/2002 | Metzger |
| 5,643,272 | A | 7/1997 | Haines | 6,430,434 B1 | 8/2002 | Mittelstadt |
| 5,643,402 | A | 7/1997 | Mumme | 6,436,145 B1 | 8/2002 | Miller |
| 5,649,928 | A | 7/1997 | Grundei | 6,443,991 B1 | 9/2002 | Running |
| 5,653,714 | A | 8/1997 | Dietz | 6,458,128 B1 | 10/2002 | Schulze |
| 5,658,293 | A | 8/1997 | Vanlaningham | 6,470,207 B1 | 10/2002 | Simon |
| 5,667,511 | A | 9/1997 | Vendrely | 6,475,241 B2 | 11/2002 | Pappas |
| 5,681,354 | A | 10/1997 | Eckhoff | 6,477,400 B1 | 11/2002 | Barrick |
| 5,682,886 | A | 11/1997 | Delp | 6,482,409 B1 | 11/2002 | Lobb |
| 5,690,632 | A | 11/1997 | Schwartz | 6,485,519 B2 | 11/2002 | Meyers |
| 5,690,635 | A | 11/1997 | Matsen, III | 6,491,699 B1 | 12/2002 | Henderson |
| 5,690,637 | A | 11/1997 | Wen | 6,491,726 B2 | 12/2002 | Pappas |
| 5,697,935 | A | 12/1997 | Moran | 6,500,208 B1 | 12/2002 | Metzger |
| 5,702,458 | A | 12/1997 | Burstein | 6,506,215 B1 | 1/2003 | Letot |
| 5,723,016 | A | 3/1998 | Minns | 6,520,964 B2 | 2/2003 | Tallarida |
| 5,725,530 | A | 3/1998 | Popken | 6,554,838 B2 | 4/2003 | McGovern |
| 5,728,162 | A | 3/1998 | Eckhoff | 6,575,980 B1 | 6/2003 | Robie |
| 5,755,801 | A | 5/1998 | Walker | 6,579,290 B1 | 6/2003 | Hardcastle |
| 5,755,803 | A | 5/1998 | Haines | 6,595,997 B2 | 7/2003 | Axelson |
| 5,755,804 | A | 5/1998 | Schmotzer | 6,620,198 B2 | 9/2003 | Burstein |
| 5,766,257 | A | 6/1998 | Goodman | 6,623,526 B1 | 9/2003 | Lloyd |
| 5,769,855 | A | 6/1998 | Bertin | 6,645,251 B2 | 11/2003 | Salehi |
| 5,769,899 | A | 6/1998 | Schwartz | 6,679,917 B2 | 1/2004 | Ek |
| 5,776,200 | A | 7/1998 | Johnson | 6,685,711 B2 | 2/2004 | Axelson |
| 5,782,921 | A | 7/1998 | Colleran | 6,694,168 B2 | 2/2004 | Traxel |
| 5,782,925 | A | 7/1998 | Collaz | 6,694,768 B2 | 2/2004 | Lu |
| 5,799,055 | A | 8/1998 | Peshkin | 6,695,848 B2 | 2/2004 | Haines |
| 5,800,552 | A | 9/1998 | Forte | 6,697,664 B2 | 2/2004 | Kienzle |
| 5,810,827 | A | 9/1998 | Haines | 6,697,768 B2 | 2/2004 | Lue |
| 5,824,100 | A | 10/1998 | Kester | 6,701,174 B1 | 3/2004 | Krause |
| 5,824,102 | A | 10/1998 | Buscayret | 6,702,821 B2 | 3/2004 | Bonutti |
| 5,824,105 | A | 10/1998 | Ries | 6,711,432 B1 | 3/2004 | Krause |
| 5,871,545 | A | 2/1999 | Goodfellow | 6,725,080 B2 | 4/2004 | Melkent |
| 5,871,546 | A | 2/1999 | Colleran | 6,755,563 B2 | 6/2004 | Wahlig |
| 5,879,354 | A | 3/1999 | Haines | 6,755,835 B2 | 6/2004 | Schultheiss |
| 5,879,392 | A | 3/1999 | McMinn | 6,755,864 B1 | 6/2004 | Brack |
| 5,906,643 | A | 5/1999 | Walker | 6,672,224 B2 | 7/2004 | Tallarida |
| 5,908,424 | A | 6/1999 | Bertin | 6,764,516 B2 | 7/2004 | Pappas |
| 5,925,049 | A | 7/1999 | Gustilo | 6,770,097 B2 | 8/2004 | Leclercq |
| 5,935,173 | A | 8/1999 | Roger | 6,773,461 B2 | 8/2004 | Meyers |
| 5,944,758 | A | 8/1999 | Mansat | 6,783,550 B2 | 8/2004 | MacArthur |
| 5,954,770 | A | 9/1999 | Schmotzer | 6,796,988 B2 | 9/2004 | Melkent |
| 5,980,526 | A | 11/1999 | Johnson | 6,827,723 B2 | 12/2004 | Carson |
| 5,986,169 | A | 11/1999 | Gjunter | 6,858,032 B2 | 2/2005 | Chow |
| 5,997,577 | A | 12/1999 | Herrington | 6,875,222 B2 * | 4/2005 | Long et al. ............ 606/172 |
| 6,039,764 | A | 3/2000 | Pottenger | 6,886,684 B2 | 5/2005 | Hacikyan |
| 6,056,754 | A | 5/2000 | Haines | 6,898,858 B1 | 5/2005 | Spell |
| 6,059,788 | A | 5/2000 | Katz | 6,911,044 B2 | 6/2005 | Fell |
| 6,068,658 | A | 5/2000 | Insall | 6,916,324 B2 | 7/2005 | Sanford |
| 6,080,195 | A | 6/2000 | Colleran | 6,916,340 B2 | 7/2005 | Metzger |
| 6,083,228 | A | 7/2000 | Michelson | 6,942,627 B2 | 9/2005 | Huitema |
| 6,099,570 | A | 8/2000 | Livet | 6,942,694 B2 | 9/2005 | Liddicoat |
| 6,110,182 | A | 8/2000 | Mowlai-Ashtiani | 7,018,418 B2 | 3/2006 | Amrich |
| 6,120,543 | A | 9/2000 | Meesenburg | 7,029,477 B2 | 4/2006 | Grimm |
| 6,132,468 | A | 10/2000 | Mansmann | 7,048,741 B2 | 5/2006 | Swanson |
| 6,139,581 | A | 10/2000 | Engh | 7,077,867 B1 | 7/2006 | Pope |
| 6,165,223 | A | 12/2000 | Metzger | 7,104,966 B2 | 9/2006 | Shilber |

| | | |
|---|---|---|
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,247,657 B2 | 7/2007 | Prager |
| 7,326,252 B2 | 2/2008 | Otto |
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 7,922,771 B2 | 4/2011 | Otto |
| 2001/0018615 A1 | 8/2001 | Biegun |
| 2001/0044627 A1* | 11/2001 | Justin ............................ 606/72 |
| 2001/0049558 A1 | 12/2001 | Liddicoat |
| 2002/0055784 A1 | 5/2002 | Burstein |
| 2002/0103541 A1 | 8/2002 | Meyers |
| 2002/0107576 A1 | 8/2002 | Meyers |
| 2002/0120340 A1 | 8/2002 | Metzger |
| 2002/0161447 A1 | 10/2002 | Salehi |
| 2003/0028196 A1 | 2/2003 | Bonutti |
| 2003/0055501 A1 | 3/2003 | Fell |
| 2003/0055509 A1 | 3/2003 | McCue |
| 2003/0060882 A1 | 3/2003 | Fell |
| 2003/0060883 A1 | 3/2003 | Fell |
| 2003/0060884 A1 | 3/2003 | Fell |
| 2003/0060885 A1 | 3/2003 | Fell |
| 2003/0069585 A1 | 4/2003 | Axelson |
| 2003/0069591 A1 | 4/2003 | Carson |
| 2003/0093156 A1 | 5/2003 | Metzger |
| 2003/0130665 A1 | 7/2003 | Pinczewski |
| 2003/0158606 A1* | 8/2003 | Coon et al. ................. 623/20.15 |
| 2003/0181986 A1 | 9/2003 | Buchholz |
| 2003/0208122 A1 | 11/2003 | Melkent |
| 2003/0212413 A1 | 11/2003 | Wilk |
| 2004/0039396 A1 | 2/2004 | Couture |
| 2004/0044414 A1 | 3/2004 | Nowakowski |
| 2004/0122305 A1 | 6/2004 | Grimm |
| 2004/0152970 A1 | 8/2004 | Hunter |
| 2004/0153066 A1 | 8/2004 | Coon |
| 2004/0199249 A1 | 10/2004 | Fell |
| 2004/0199250 A1 | 10/2004 | Fell |
| 2004/0249467 A1 | 12/2004 | Meyers |
| 2004/0249471 A1 | 12/2004 | Bindseil |
| 2004/0267363 A1 | 12/2004 | Fell |
| 2005/0033424 A1 | 2/2005 | Fell |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2005/0283251 A1 | 12/2005 | Coon |
| 2006/0015109 A1 | 1/2006 | Haines |
| 2006/0015115 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0076514 A1 | 3/2009 | Haines |
| 2009/0082773 A1 | 3/2009 | Haines |
| 2009/0138018 A1 | 5/2009 | Haines |
| 2010/0100192 A1 | 4/2010 | Haines |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002-274214 | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

E. Marlowe Goble and Daniel F. Justin, *Minimally invasive total knee replacement: principles and technique*, Orthop. Clin. N. Am. 35 (2004) 235-245.
Whiteside Ortholoc Total Knee System: Surgical Procedure, Dow Corning Wright, pp. WMT000001-WMT000040, Jun. 1985.
Zimmer, Insall/Burstein II, *Constrained Condylar: Modular Knee System*, 35 pages, copyright 1989.
File History for U.S. Appl. No. 12/187,210, filed Aug. 6, 2008.
File History for U.S. Appl. No. 11/075,842, filed Mar. 8, 2005.
File History for U.S. Appl. No. 11/075,828, filed Mar. 8, 2005.
File History for U.S. Appl. No. 11/075,836, filed Mar. 8, 2005.
File History for U.S. Appl. No. 11/075,840, filed Mar. 8, 2005.
U.S. Appl. No. 11/036,584, Inventor: Haines, filed Jan. 14, 2005.
U.S. Appl. No. 12/171,843, Inventor: Haines, filed Jul. 11, 2008.
U.S. Appl. No. 11/825,857, Inventor: Haines, filed Jul. 9, 2007.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
U.S. Appl. No. 12/638,692, filed Dec. 15, 2009, Haines.
Freeman Samuelson, *Total Knee System*, published by Biomet, Inc., 1994 ("Biomet Brochure") (Attached as Exhibit F).
Freeman, *Mark II Total Knee Replacement System*, published 1985 (Attached as Exhibit G).
Protek F/S Modular Total Knee Replacement System, pp. 1-57, published by Protek in Jan. 1991 (Attached as Exhibit H).
*Low Contact Stress Meniscal Bearing Unicompartmental Knee Replacement: Long-Term Evaluation of Cemented and Cementless Results*, Journal of Orthopaedic Rheumatology (presented at the 57$^{th}$ Annual American Academy of Orthopaedic Surgeons Meetings, New Orleans, LA, Feb. 11, 1990), Bates Number DEP00004096-DEP00004107.
N.J. Unicompartmental Knee, Dated Sep. 15, 1989, Bates Number DEP00004108-DEP00004116.
Buechel, Frederick F., *NJ LCS Unicompartmental Knee System with Porocoat*, dated Oct. 24, 1994, Bates Number DEP000004117-DEP00004130.
Buechel, Frederick F. *NJ LCS Unicompartmental Knee System with Porocoat*, 1994, Bates Number DEP00004131-DEP00004141.
Buechel, Frederick F. *NJ LCS Unicompartmental Knee System with Porocoat*, 1994, Bates No. DEP00004142-DEP00004152.
Engh, et al., *The AMK Total Knee System, Design Rationale and Surgical Procedure*, dated 1989, Bates Number DEP00004153-DEP00004201.
*Advertising Proteck Mark II PCR Total Knee Replacement System*, Journal of Bone and Joint Surgery, 1987, Bates No. DEP00004202-DEP00004230.
Protek, *Parts Brochure for Mark II Protek*, 1987, Bates Number DEP00004231-DEP00004235.
Chapman, Michael W., *Operative Orthopaedics*, vol. 1, Published by J.B. Lipponcott Co., Philadelphia, dated 1988, Bates Number DEP00004236- DEP00004247.
American Academy of Orthopaedic Surgeons, *Flyer from 57$^{th}$ Annual American Academy of Orthopaedic Surgeons Meeting*, Februay 13, 1990, Bates Number DEP00004248-DEP00004251.
Crossett et al., *AMK Congruency Instrument System, Surgical Technique*, dated 1997, Bates Number DEP00004252-DEP00004267.
Engh et al., *AMK Surgical Technique*, Bates Number DEP00004268-DEP00004298, dated 1989.
Engh et al., *AMK Surgical Technique*, Bates Number DEP00004299-DEP0004329, dated 1989.
Crenshaw, A.H., *Campbell's Operative Orthopaedics*, 4$^{th}$ Edition, vol. 1, Bates Number DEP00004330-DEP00004333, dated 1963.
Howmedica, *Duraconcept, Design Concepts of the Duracon Total Knee System*, Bates Number DEP00004337-DEP00004337, dated 1993.
Freeman et al., *Total Knee System*, Bates Number DEP00004350-DEP00004361, Published prior to Jun. 7, 1994.
freeman et al., *F/S Modular Total Knee Replacement System-SICOT*, 90 Edition, Bates Number DEP00004362-DEP00004373, dated 1990.
Buechel, Frederick F., *Howmedica Product Catalog*, Bates Number DEP 00004374-DEP00004375, dated 1994.
Massarella, Antony, *Interax Bulletin, No. 6, Tibial Intramedullary Alignment Surgical Technique*, Bates Number DEP00004387-DEP0000- 4390, dated Feb. 23, 1994.
Desjardins et al., *Interax Operative Technique*, Bates Number DEP00004391-DEP00004411, dated 1994.
Desjardins et al., *Interax Total Knee Operative Technique: Monogram Total Knee Instruments*, Bates Number DEP00004412-DEP00004432, dated 1993.
Howmedica, *Interax Tibial IM*, Bates Number DEP00004433-DEP00004433, dated 1994.
Depuy, *LCS Uni PMA Data from FDA Website*, Bates Number DEP00004434-DEP00004434, dated 1991.
Briard et al., *LCS Uni Unicompartmental Knee System with Porocoat*, Bates Number DEP00004452-DEP00004462, dated 1991.
Freeman et al., *Mark II Total Knee Replacement System*, Bates Number DEP00004463-DEP00004492, dated 1985.
Buechel, Frederick F., *NJ LCS Unicompartmental Knee System with Porocoat*, Bates Number DEP00004493-DEP00004503, dated 1994.
Chapman, Michael W. *Operative Orthopaedics*, vol. 3, 2$^{nd}$Edition, Published by J.B. Lipponcott Co., Bates Number DEP00004504-DEP00004508, dated 1993.
Biomet, *Oxford Meniscal Knee Phase II Unicompartmental Replacement*, Bates Number DEP00004509-DEP00004515, Published prior to Jun. 7, 1994.
Scott et al., *P.F.C. Sigma Unicompartmental Knee System*, Bates Number DEP00004531-DEP00004539, dated 1998.
Freeman et al., *F/S Modular Total Knee Replacement System*, Bates Number DEP00004540-DEP00004596, dated 1990.
Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates Number DEP00004752-DEP00004763.
Scott et al., *Unicompartmental and High Tibial Osteotomy for Osteoarthritis of the Knee*, Journal of Bone and Joint Surgery, vol. 63-A, No. 4, Apr. 1, 1981, Bates Number DEP00004764-DEP00004775.
Thornhill, Thomas S., *Unicompartmental Knee Arthroplasty Clinical Orthopaedics and Related Research*, No. 205, Apr. 1, 1986, pp. 121-131, Bates Number DEP00004776-DEP00004791.
Forst et al., *A Special jg for Tibial Resection for the Implantation of GSB-Knee-Prostheses in Problematic cases*, pp. 162-166, dated Jun. 1, 1984, Bates Number DEP00004838-DEP00004842.
Ingillis et al., *Revision Total Knee Replacement Techniques in Orthopedics*, dated Apr. 1, 1990, Bates Number DEP00005583-DEP00005592.
Uvehammer et al., "In Vivo Kinematics of Total Knee Arthroplasty: Concave Versus Posterior-Stabilised Tibial Joint Surface", vol. 82-B, No. 4, May 2000, pp. 499-505.

\* cited by examiner

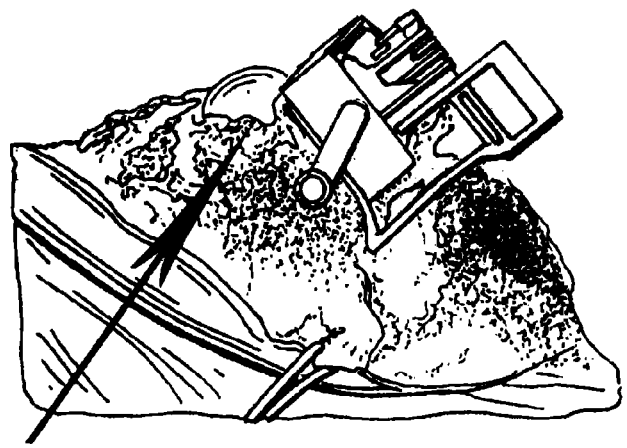
FEMUR  *Fig.3A*
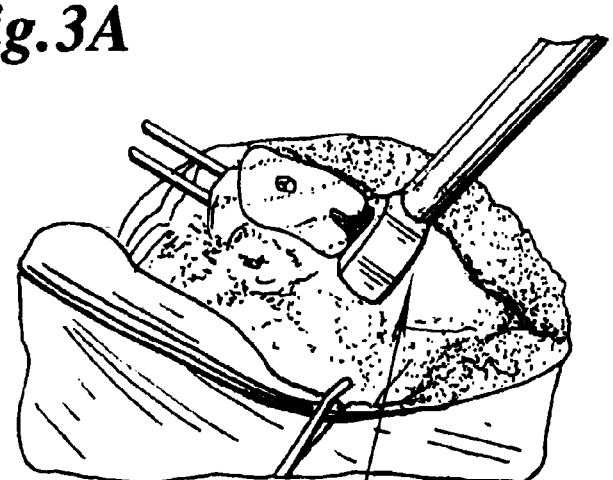
*Fig.3B*  TIBIA
PATELLA
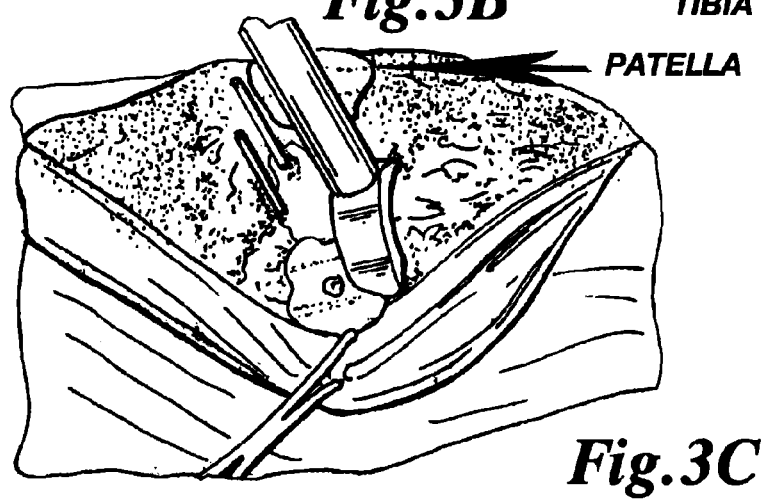
*Fig.3C*

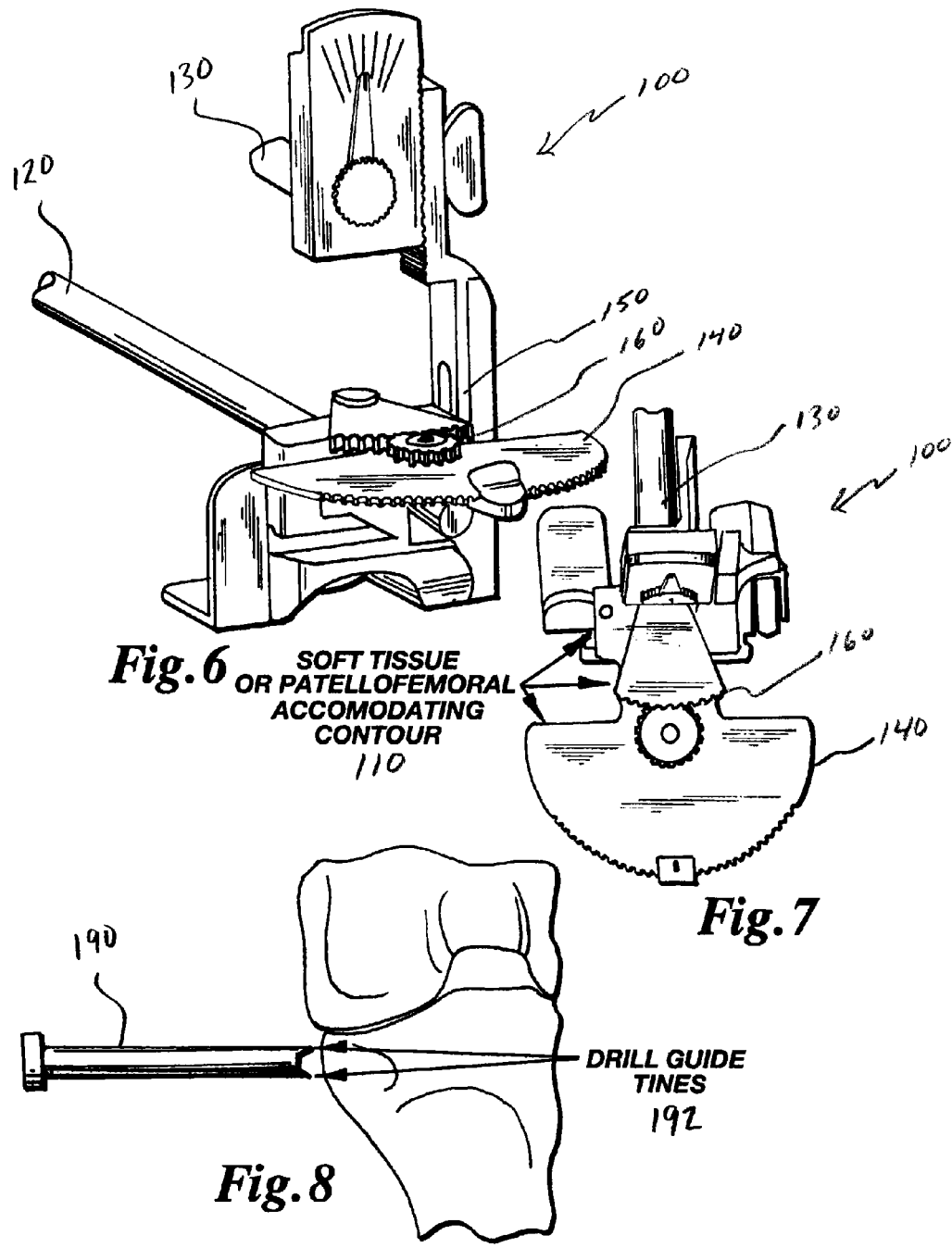

DRILL
194

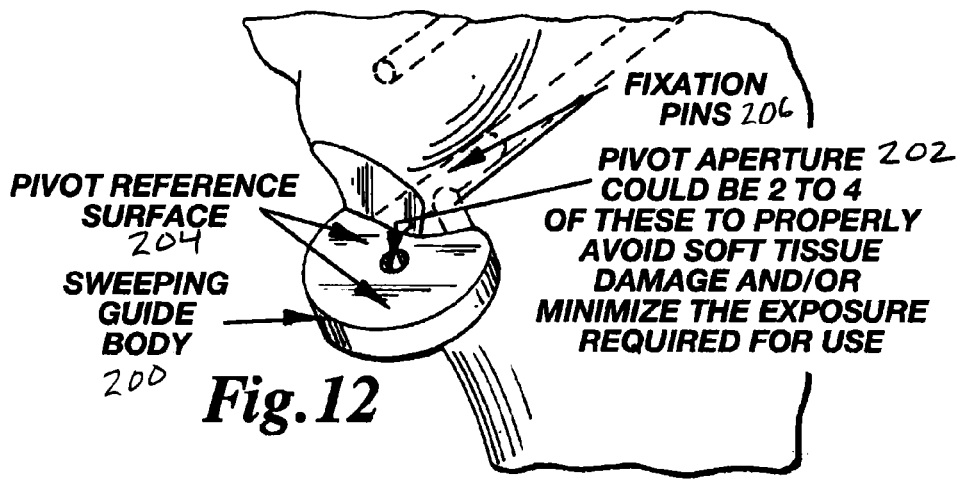
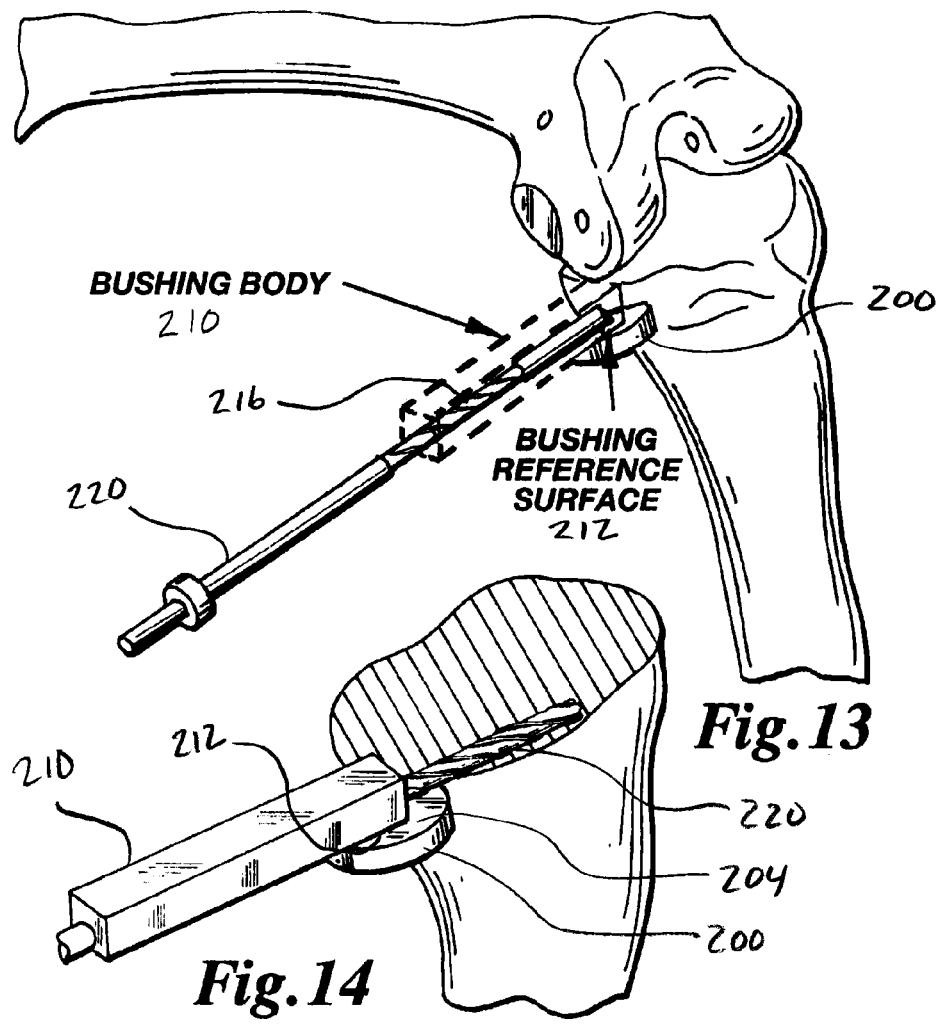

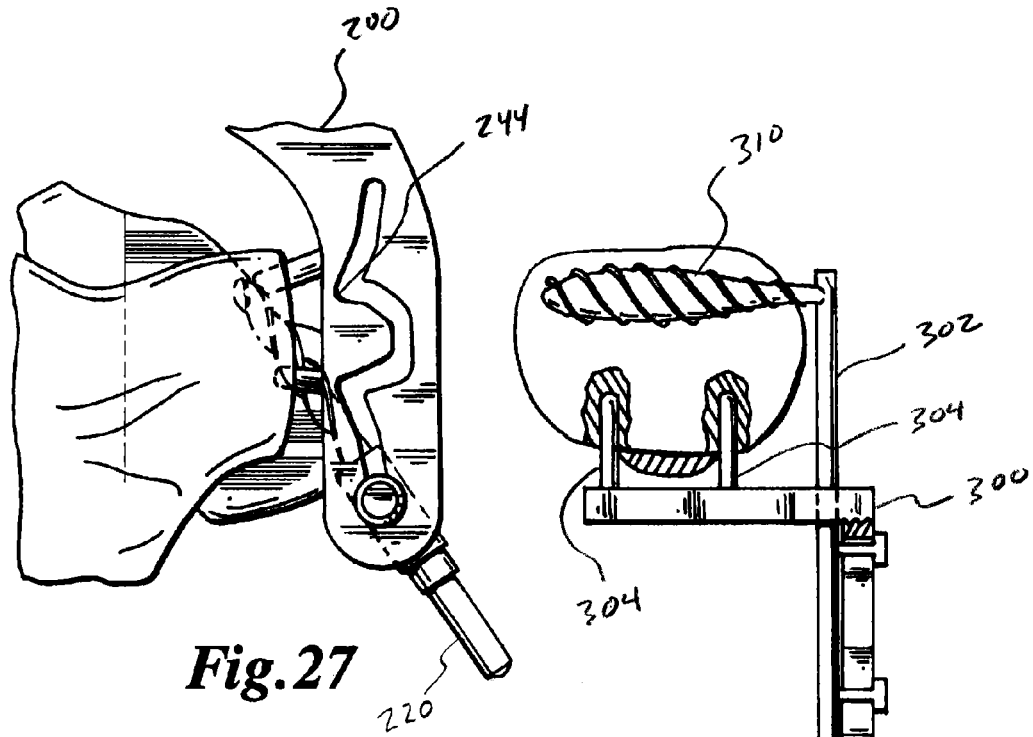
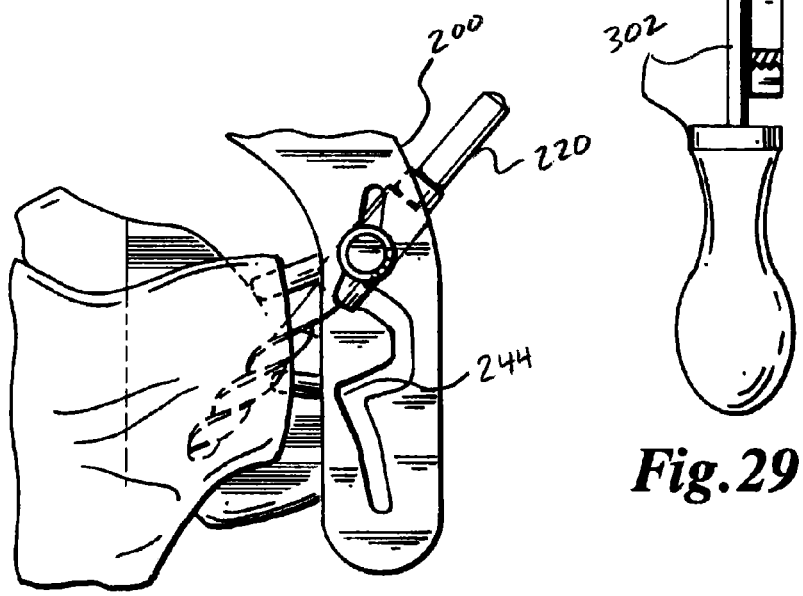
Fig.27
Fig.29
Fig.28

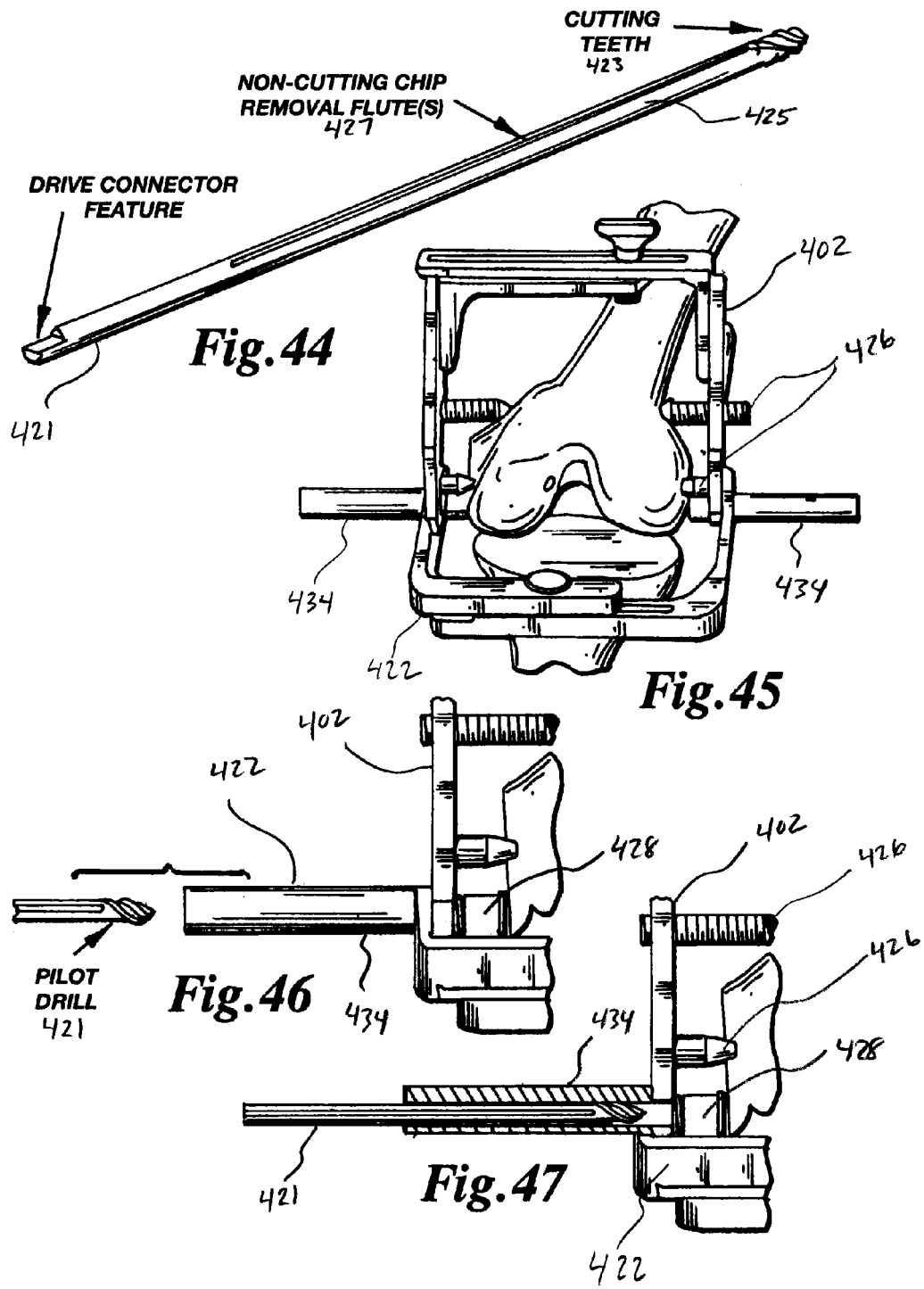

SIDE CUTTING DRILL 420

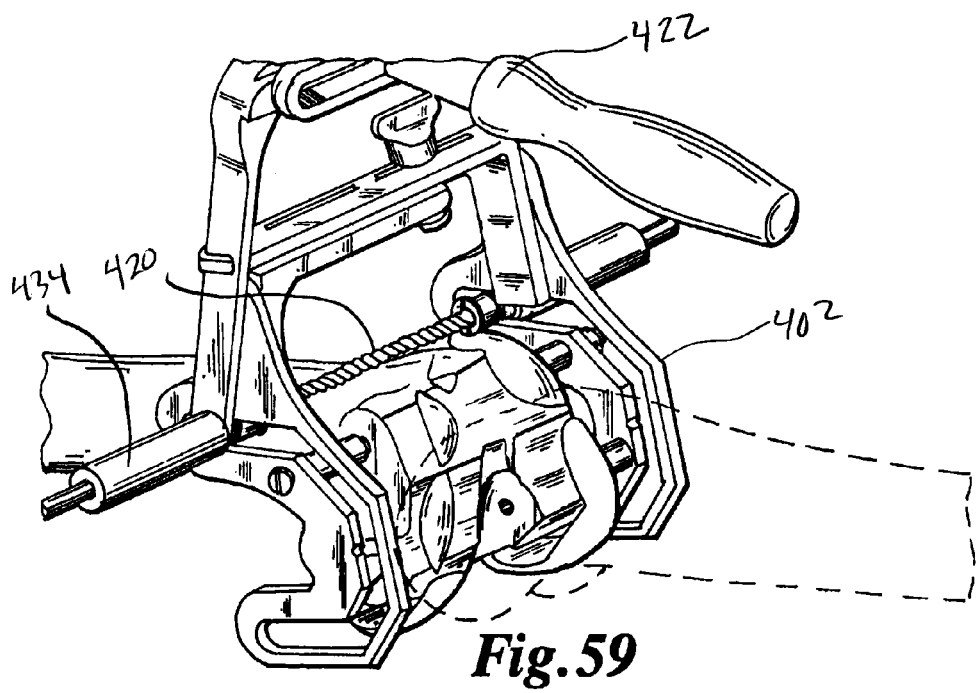
*Fig.59*
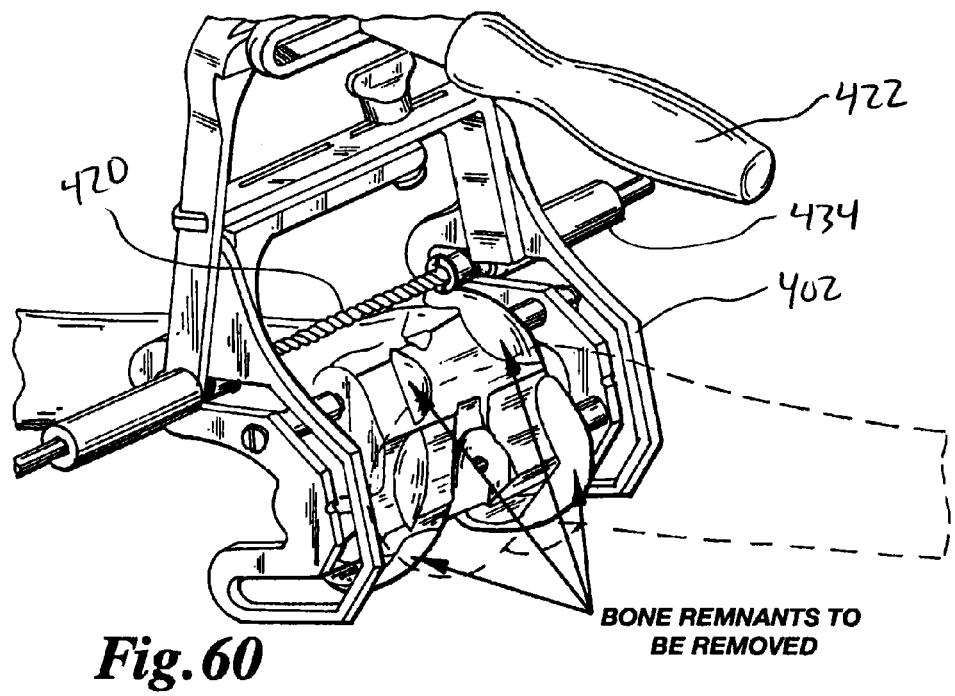
*Fig.60*   BONE REMNANTS TO BE REMOVED

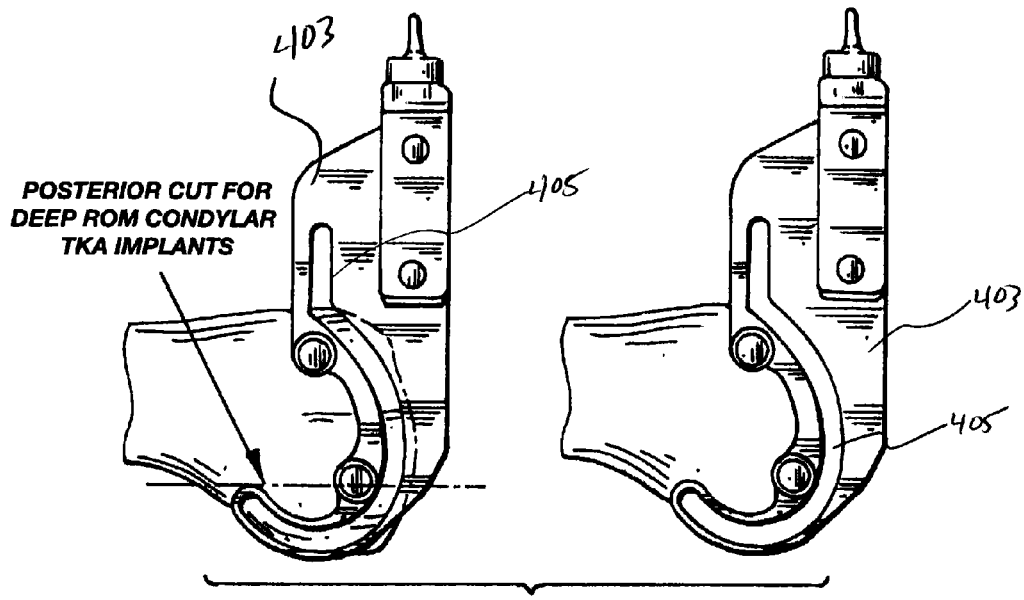
*Fig.61*
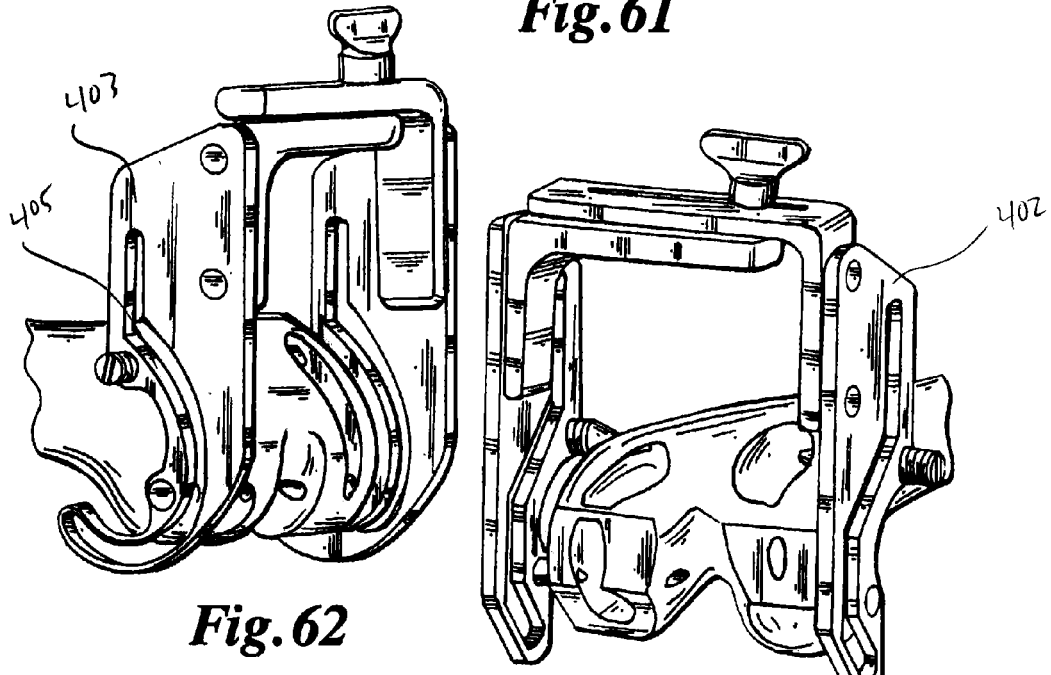
*Fig.62*
*Fig.63*

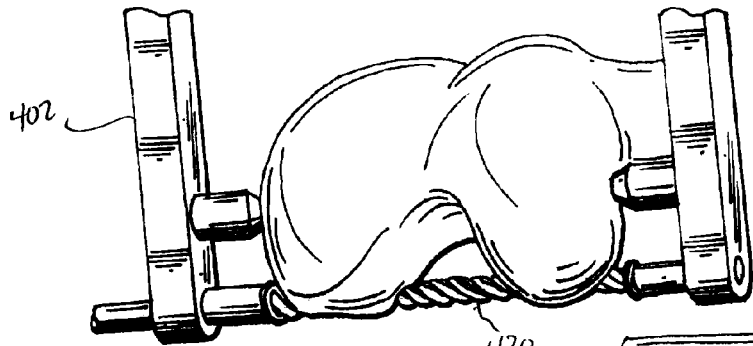

Fig. 78

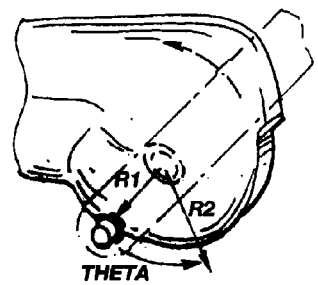

Fig. 79

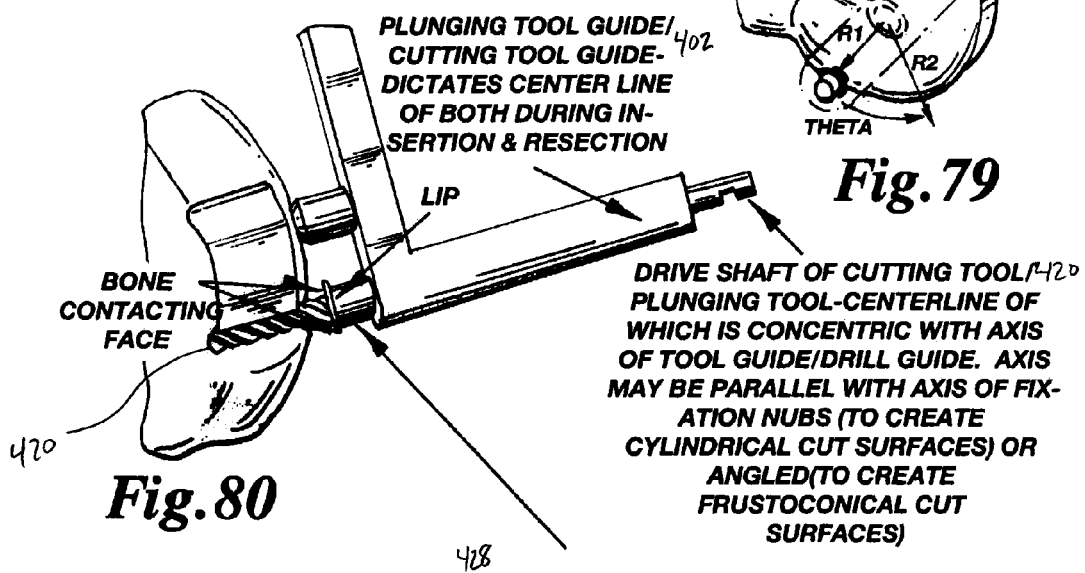

Fig. 80

PLUNGING TOOL GUIDE/ CUTTING TOOL GUIDE- DICTATES CENTER LINE OF BOTH DURING INSERTION & RESECTION

LIP

BONE CONTACTING FACE

DRIVE SHAFT OF CUTTING TOOL/ PLUNGING TOOL-CENTERLINE OF WHICH IS CONCENTRIC WITH AXIS OF TOOL GUIDE/DRILL GUIDE. AXIS MAY BE PARALLEL WITH AXIS OF FIXATION NUBS (TO CREATE CYLINDRICAL CUT SURFACES) OR ANGLED(TO CREATE FRUSTOCONICAL CUT SURFACES)

SOFT TISSUE 'SLEEVE'-PERHAPS SPRING LOADING TO BIAS IT INTO CONTACT WITH BONE TO PREVENT SOFT TISSUE CONTACT WITH CUTTING SURFACES OF CUTTING TOOL. SLEEVE COULD/SHOULD BE ARTICULATED WITH MILLING HANDLE TO REMAIN IN CONTACT WITH BONE AS MILL OR OTHER CUTTER TRAVERSES ITS OR THE CUTTING PATH. THE LITTLE LIP, PERHAPS A BIGGER LIP, COULD HELP RETAIN THE BONE CONTACTING FACE BETWEEN BONE & CAPSULE/LIGAMENT/SOFT TISSUE DURING CUTTING. IN THIS MANNER, CONTACT BETWEEN THE CUTTING TOOL AND SOFT TISSUE, AND THEREBY ANY TRAUMA BEYOND INSERTION OF THE TOOL THROUGH THE SOFT TISSUE AND ACROSS THE BONE, MAY BE AVOIDED.

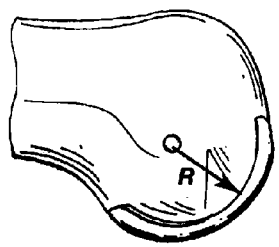
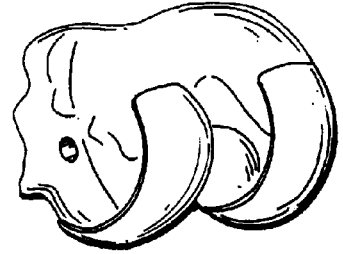
*Fig.81*          *Fig.82*
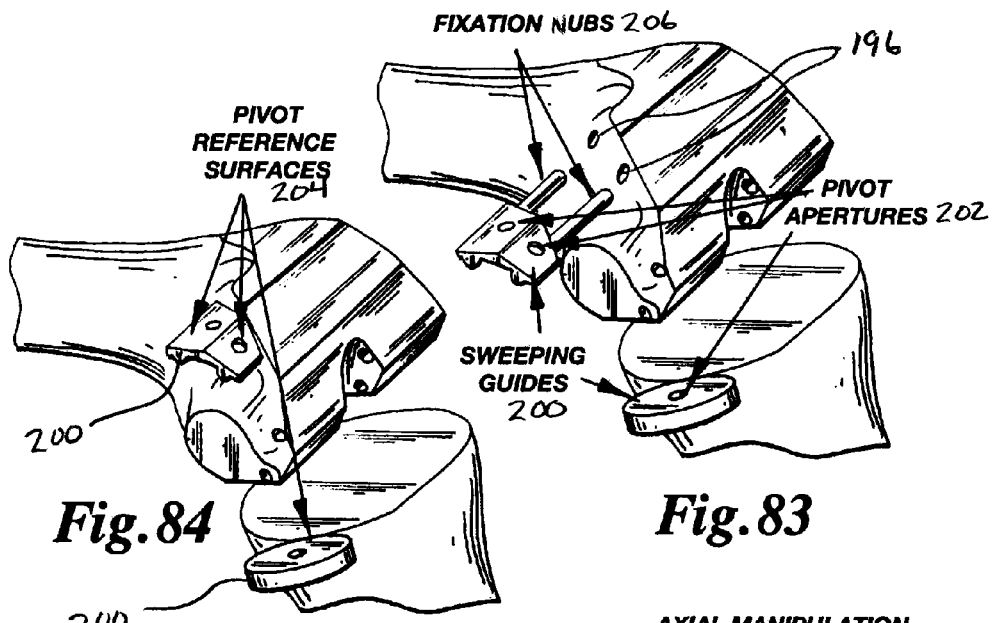
*Fig.83*    *Fig.84*    *Fig.85*

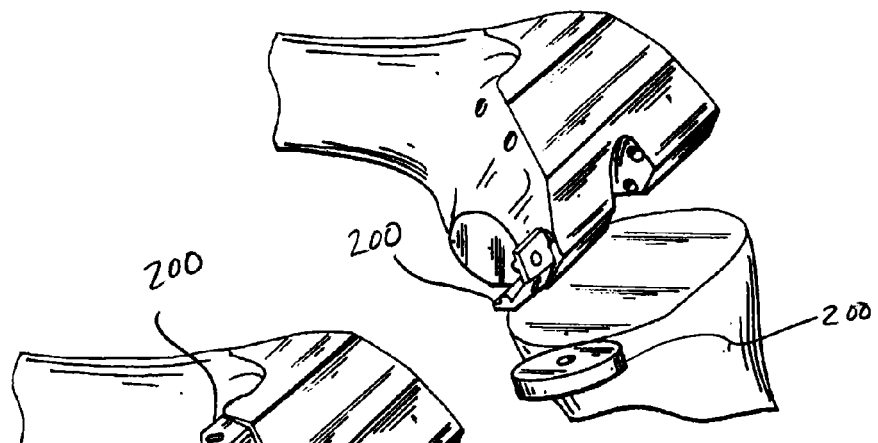
*Fig.86*
*Fig.87*
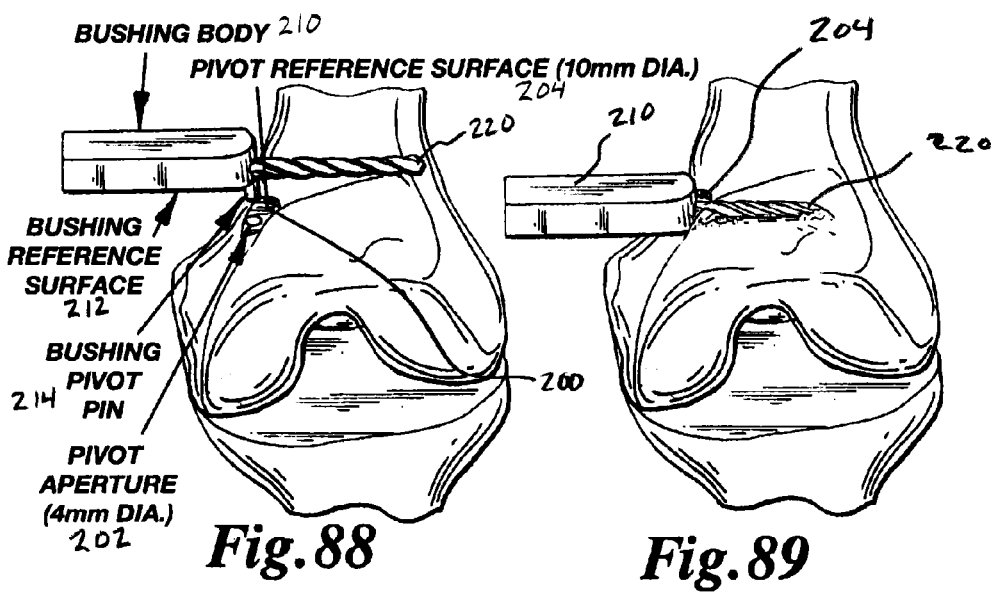
*Fig.88*   *Fig.89*

METHODS AND APPARATUS FOR IMPROVED DRILLING AND MILLING TOOLS FOR RESECTION

CLAIM TO PRIORITY

The present invention claims priority to U.S. Provisional Application No. 60/551,262, filed Mar. 8, 2004, entitled, "METHODS AND APPARATUS FOR IMPROVED DRILLING AND MILLING TOOLS FOR RESECTION," and claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and claims priority to U.S. Provisional Application No. 60/551,078, filed Mar. 8, 2004, entitled, "METHODS AND APPARATUS FOR MINIMALLY INVASIVE RESECTION," and claims priority to U.S. Provisional Application No. 60/551,096, filed Mar. 8, 2004, entitled, "METHODS AND APPARATUS FOR ENHANCED RETENTION OF PROSTHETIC IMPLANTS," and claims priority to U.S. Provisional Application No. 60/551,631, filed Mar. 8, 2004, entitled, "METHODS AND APPARATUS FOR CONFORMABLE PROSTHETIC IMPLANTS," and claims priority to U.S. Provisional Application No. 60/551,307, filed Mar. 8, 2004, entitled, "METHODS AND APPARATUS FOR IMPROVED CUTTING TOOLS FOR RESECTION," and claims priority to U.S. Provisional Application No. 60/551,160, filed Mar. 8, 2004, entitled, "METHODS AND APPARATUS FOR IMPROVED PROFILE BASED RESECTION," and is a continuation-in-part of U.S. patent application Ser. No. 11/036,584, filed Jan. 14, 2005, entitled, "METHODS AND APPARATUS FOR PINPLASTY BONE RESECTION," and is a continuation-in-part of U.S. patent application Ser. No. 11/049,634, filed Feb. 2, 2005, entitled, "METHODS AND APPARATUS FOR WIREPLASTY BONE RESECTION," which claims priority to U.S. Provisional Application No. 60/536,320, filed Jan. 14, 2004, and is a continuation-in-part of U.S. patent application Ser. No. 11/049,634, filed Feb. 3, 2005, entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to methods and apparatus for improved drilling and milling tools for resection and arthroplasty.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement and other forms of bone resection for over 30 years. Unfortunately, present approaches to using existing planar or non-planar saw blade instrumentation systems all possess certain limitations and liabilities.

Perhaps the most critical factor in the clinical success of any bone resection for the purpose of creating an implant surface on the bone is the accuracy of the implant's placement. This can be described by the degrees of freedom associated with each implant. In the case of a total knee arthroplasty (TKA), for example, for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems for TKA, the distal resection cutting guide is positioned by drilling two long drill bits into the anterior cortex across the longitudinal axis of the bone. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking" inherent in the use of multiple alignment guides and cutting guides.

Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA and other bone resection procedures for more than 30 years, there are still reports of incidences where poor cuts result in significant gaps in the fit between the implant and the bone. Improvements in the alignment and operation of cutting tools for resecting bone surfaces are desired in order to increase the consistency and repeatability of bone resection procedures as is the improvement of prosthetic stability in attachment to bone.

One technique that has been developed to address these challenges has been the profile based resection (PBR) techniques taught, for example, by U.S. Pat. Nos. 5,514,139, 5,597,397, 5,643,272, and 5,810,827. In a preferred embodiment of the PBR technique, a side cutting tool such as a milling bit or side drill bit is used to create the desired resected surface. While the PBR technique offers many advantages over conventional resection and arthroplasty techniques, it would be desirable to provide enhancements to the PBR technique that improve the ability to address soft tissue management

SUMMARY OF THE INVENTION

The present invention provides for embodiments of milling and drilling tools and soft tissue management techniques for arthroplasty facilitating intraoperative and postoperative efficacy and ease of use. In one embodiment, resiliently biased soft tissue protective sleeves surround the side cutting tool and are interposed along the longitudinal axis of the side cutting tool adjacent each side of the bone. The soft tissue protective sleeves are biased to track along the contour of the side of the bone and prevent the side cutting tool from being exposed to soft tissue during the resection. In another embodiment, a pilot drill is initially utilized to create an initial bore in the bone to be resected. The pilot drill preferably has an end cutting arrangement and a non-cutting removal channel that minimizes the tendency of the pilot drill bit to drift off-axis as the initial bore in the bone is created. Once the initial bore is created, the pilot drill bit is withdrawn and a second side cutting tool, such as a milling bit, is then inserted into the bore to perform the desired surface resection.

The present invention utilizes a number of embodiments of cutting tools to remove boney material to create cut surfaces for prosthetic implant attachment and fixation. The overriding objects of the embodiments are to provide the ability to perform resection in very small incisions, the creation of precise and accurate cut(s), and to provide for soft tissue protection characteristics and features preventing the tool from accidentally harming soft tissue. Specifically, many of the cutting tool embodiments disclosed are either incapable or highly resistant to damaging soft tissue, or are by means disclosed prevented from coming into contact with soft tissue in the first place.

The present invention utilizes a number of embodiments of cutting guide technologies loosely or directly based on Profile Based Resection (PBR). The overriding objects of PBR technologies are to provide for significantly improved reproducibility of implant fit and alignment in a manner largely independent of the individual surgeon's manual skills, while providing for outstanding ease of use, economic, safety, and work flow performance.

The present invention utilizes a number of embodiments of alignment or drill guides to precisely and accurately determine the desired cutting guide location/orientation, thus cut surface location(s)/orientation(s), thus prosthetic implant location and orientation. The overriding objects of the embodiments are to precisely and accurately dictate the aforementioned locations and orientations while optionally enabling ease of use in conjunction with manually or Computer Assisted techniques, and while optionally enabling ease of use in minimally invasive procedures where surgical exposure and trauma are minimized.

The present invention utilizes a number of methods and apparatus embodiments of soft tissue management techniques and the devices supporting said techniques. The overriding object of these embodiments is to take advantage of the anatomy, physiology, and kinematics of the human body in facilitating clinical efficacy of orthopedic procedures.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases risk to soft tissue, incision or exposure size requirements, manual skill requirements, and/or visualization of cutting action.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 1, 2, and 3 are pictorial representations standard incision sizes or exposure required by the prior art, while

DETAILED DESCRIPTION OF THE PREFERRED EMBODIMENTS

It should be noted that, in many of the figures, the cut surface created by the cutting tool in accordance with the techniques of the present invention are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity FIGS. 1 through 4

Figure 1:
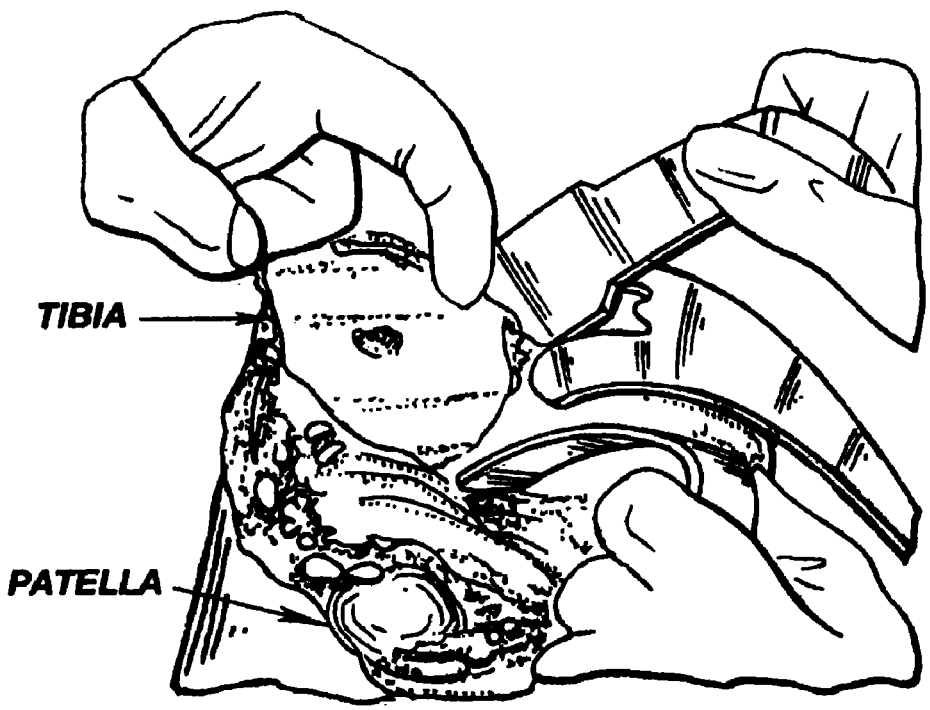
Figure 2:
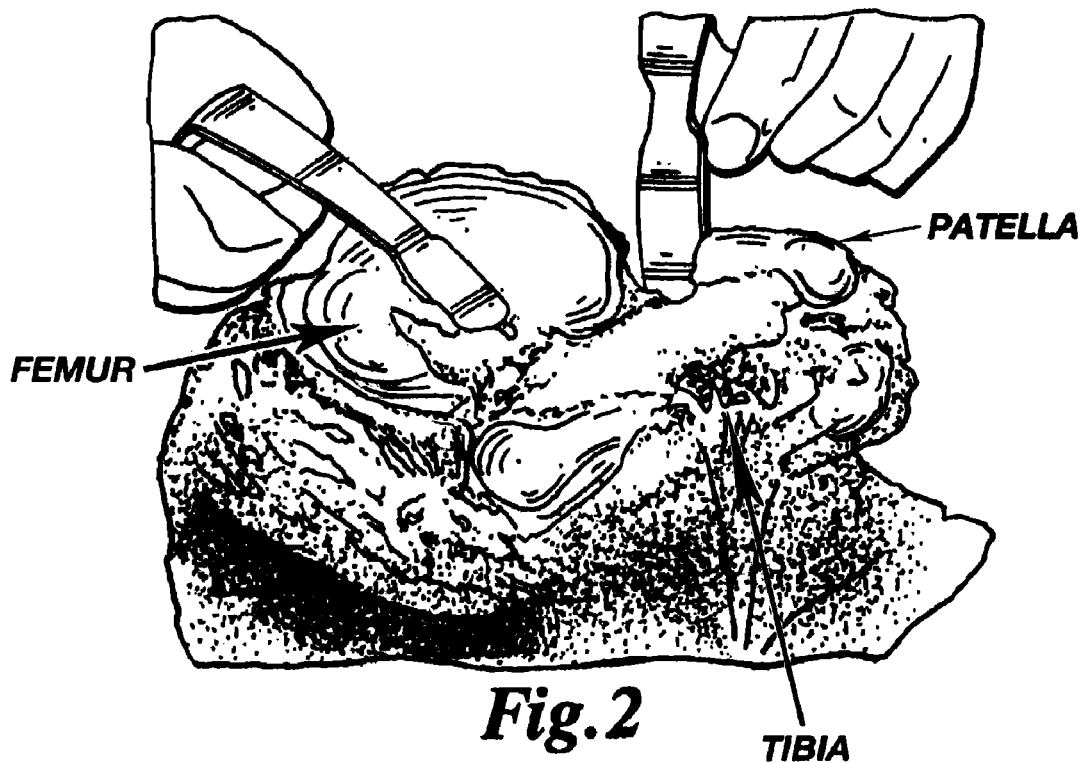
Figure 4:
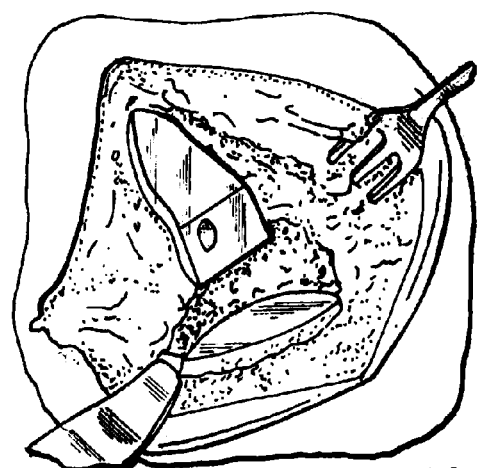
FIG. 4 is a pictorial representation or approximation of one form of surgical exposure that is desired.

FIGS. 1 and 2 show conventional surgical exposures and instrumentation being utilized. FIG. 4 shows a reduced incision currently utilized in performing the current state of the art in 'minimally invasive' Unicondylar Knee Replacement.

FIGS. 41-60

Figure 35:
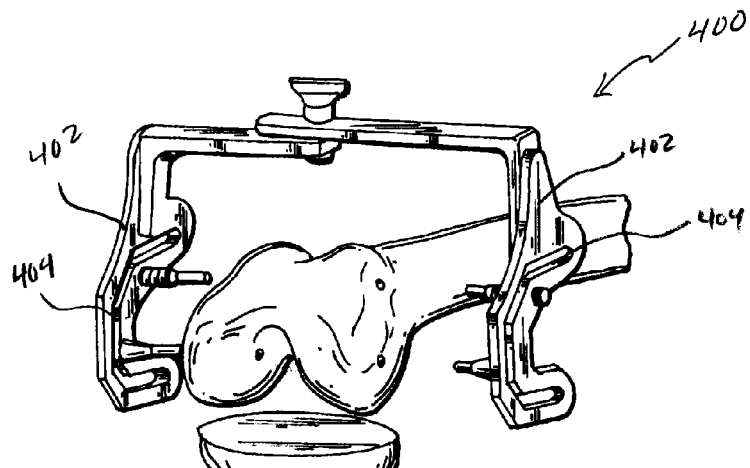
Figure 36:
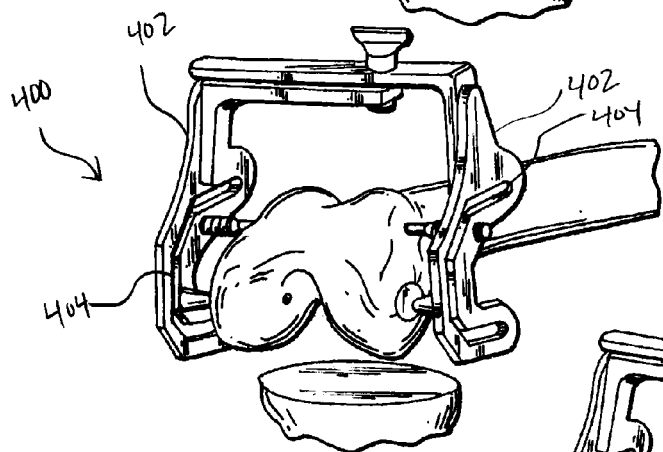
Figure 37:
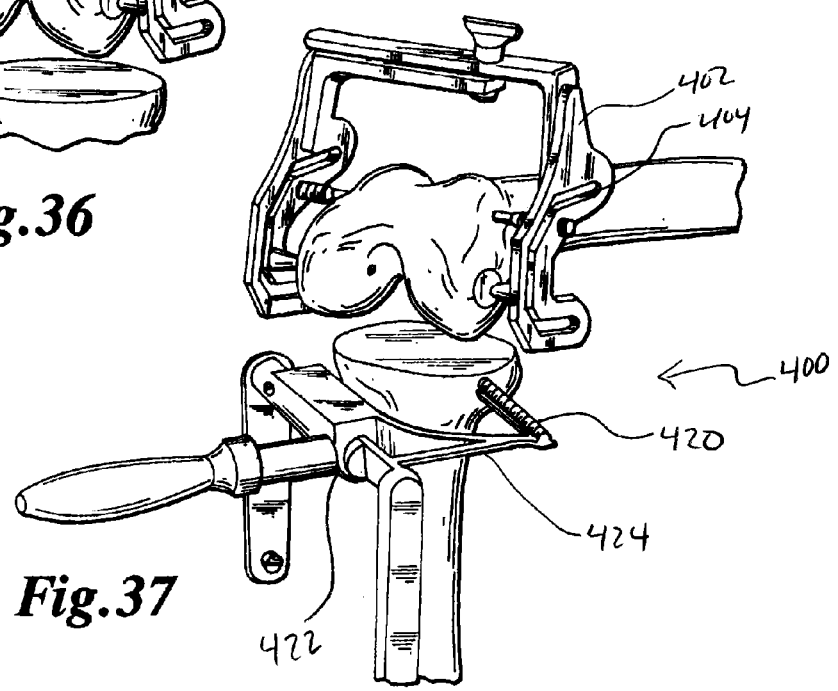
Figure 38:
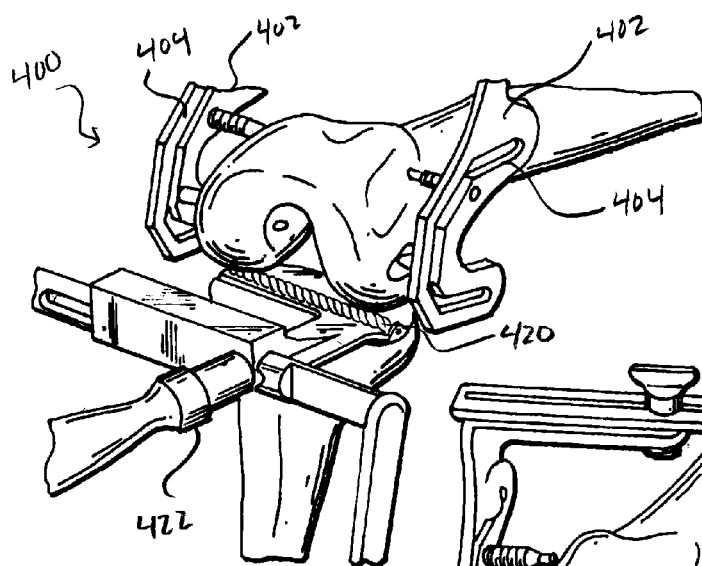
Figure 39:
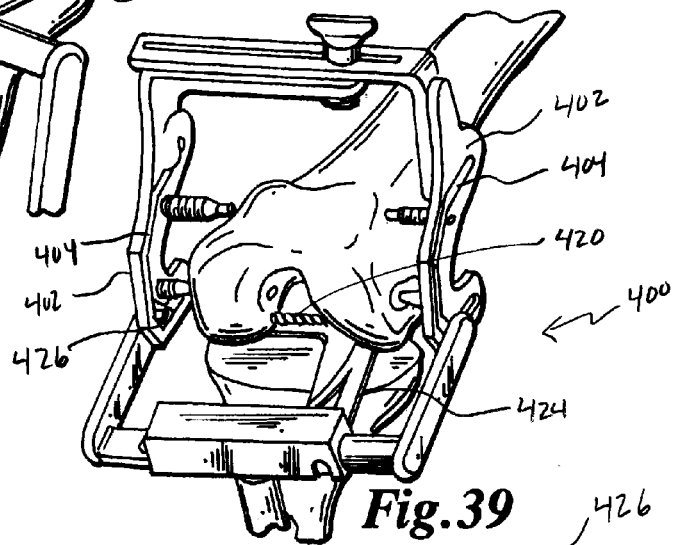
Figure 42:
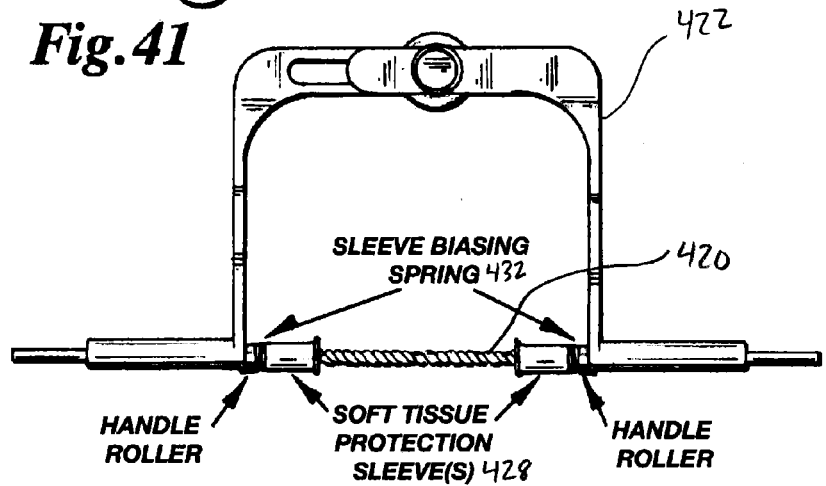
Figure 43:
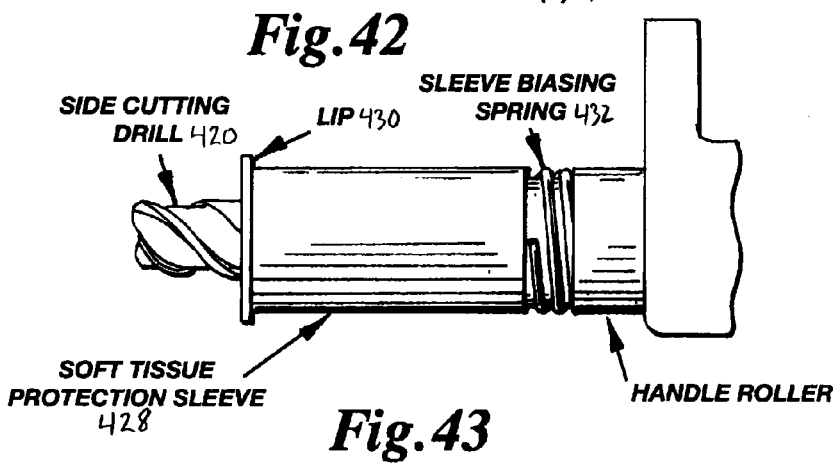
Figure 48:
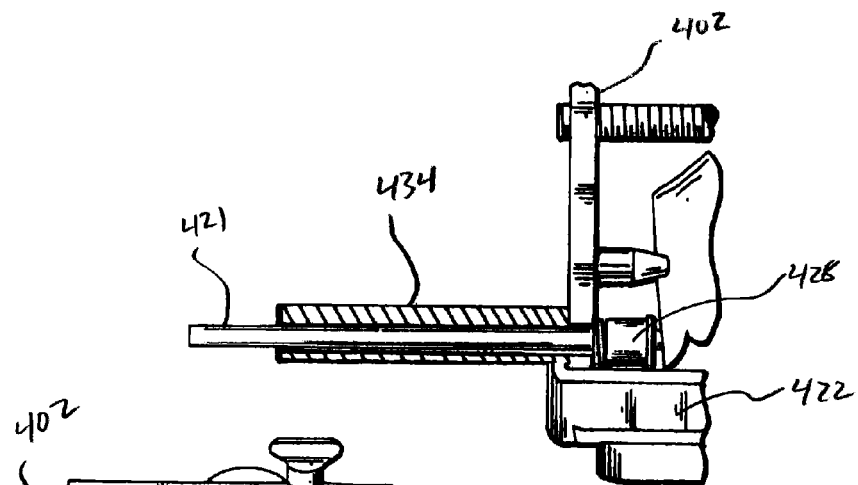
Figure 49:
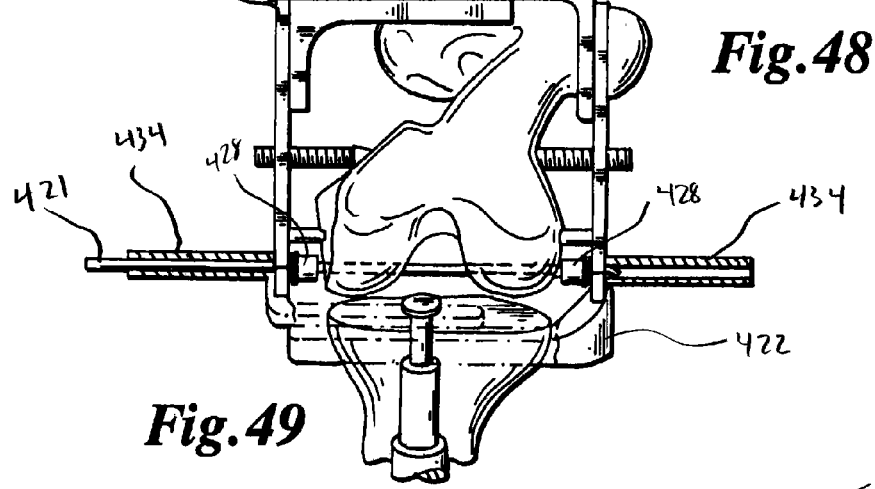
Figure 50:
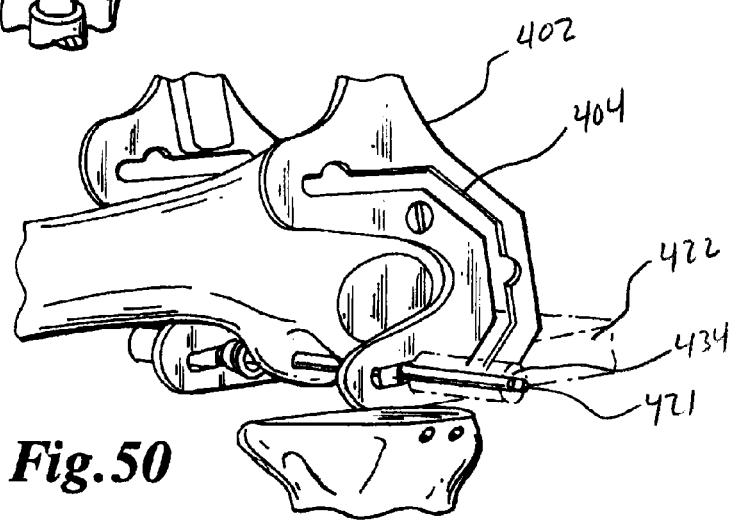
Figure 52:
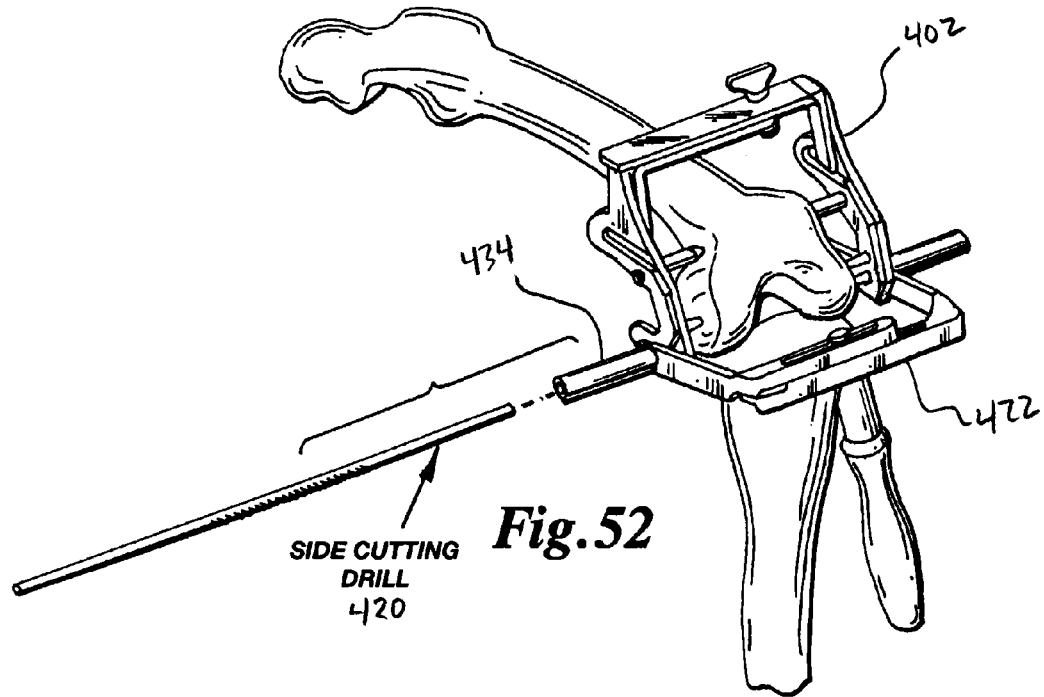
Figure 53:
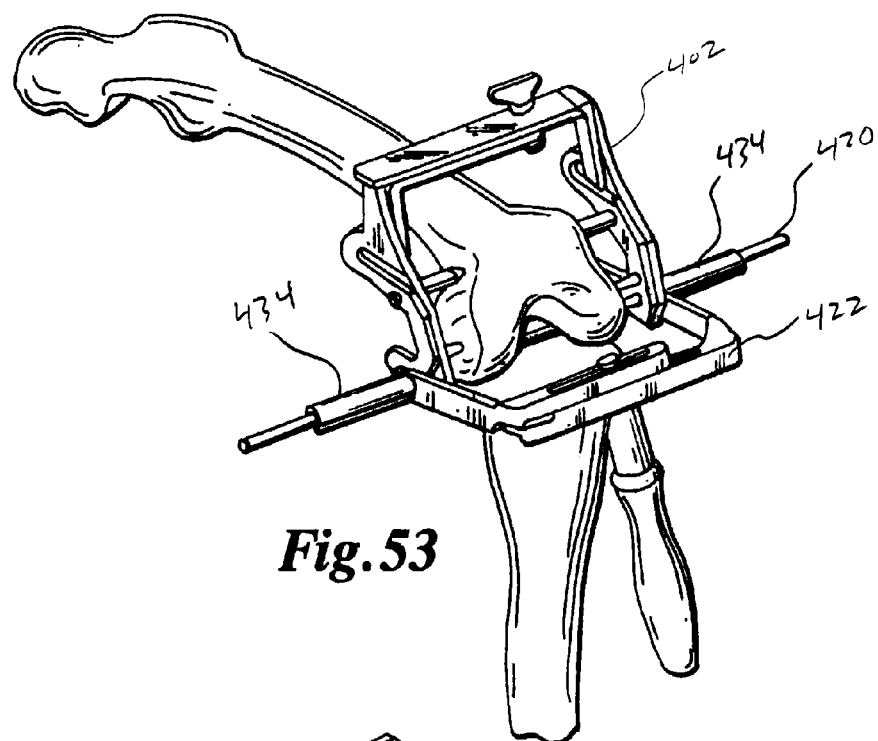
Figure 54:
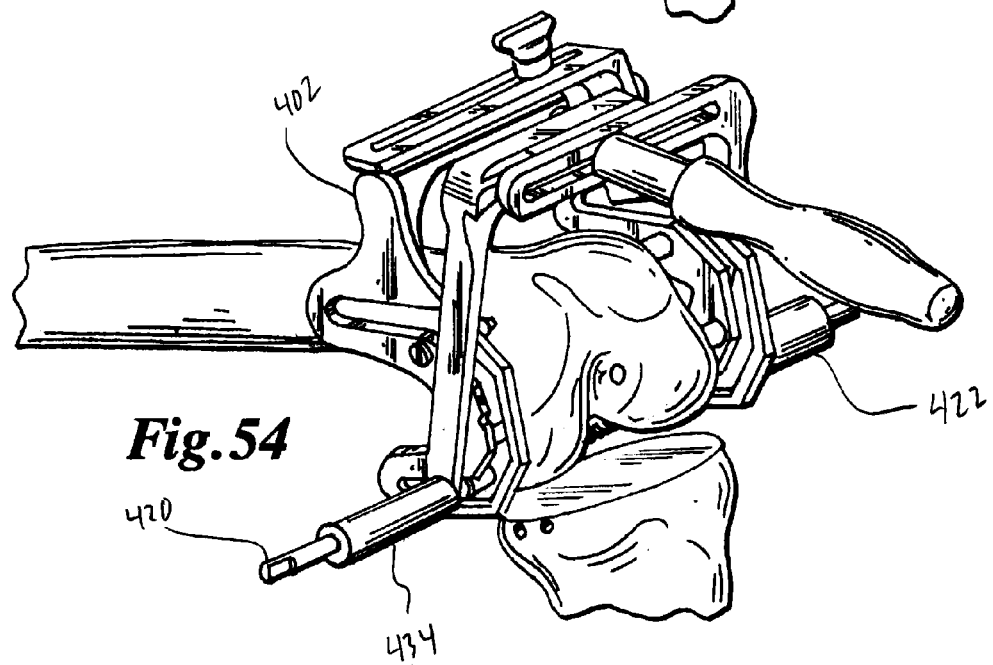
Figure 55:
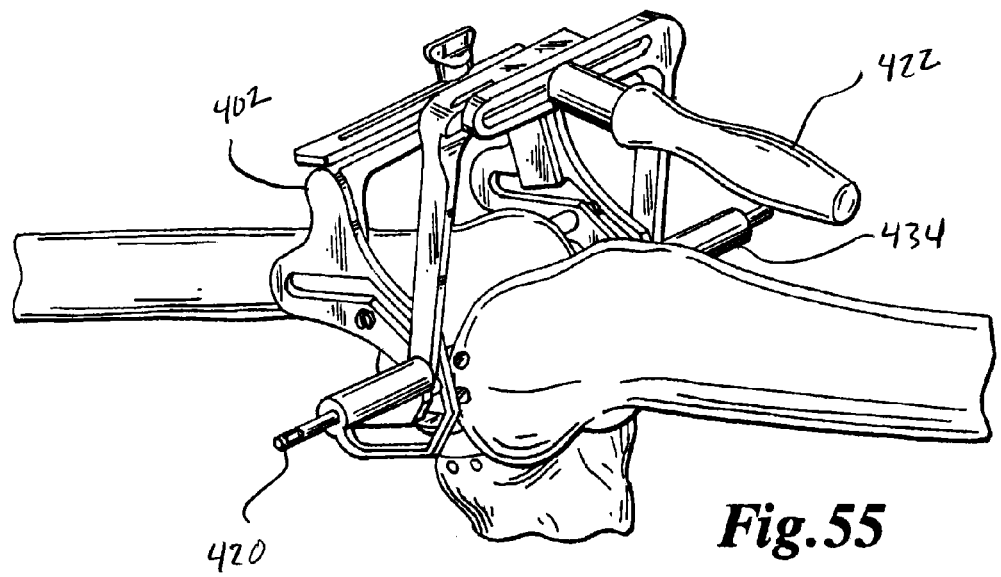
Figure 56:
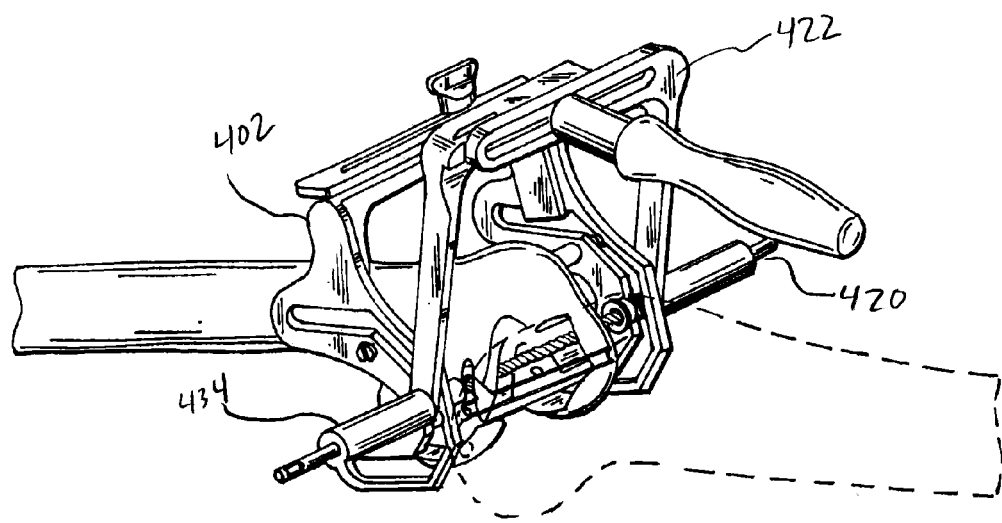
Figure 57:
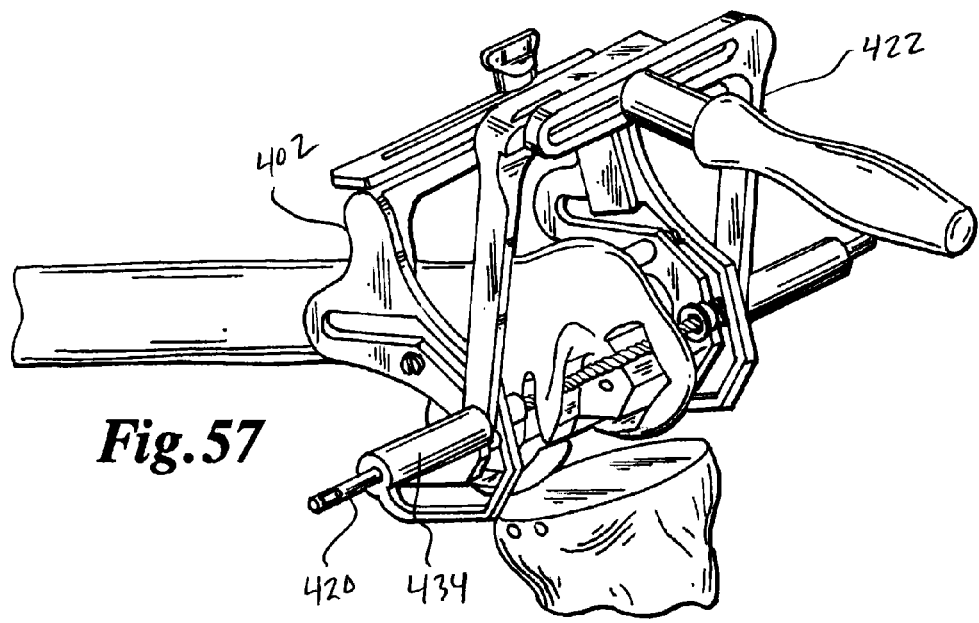
Figure 58:
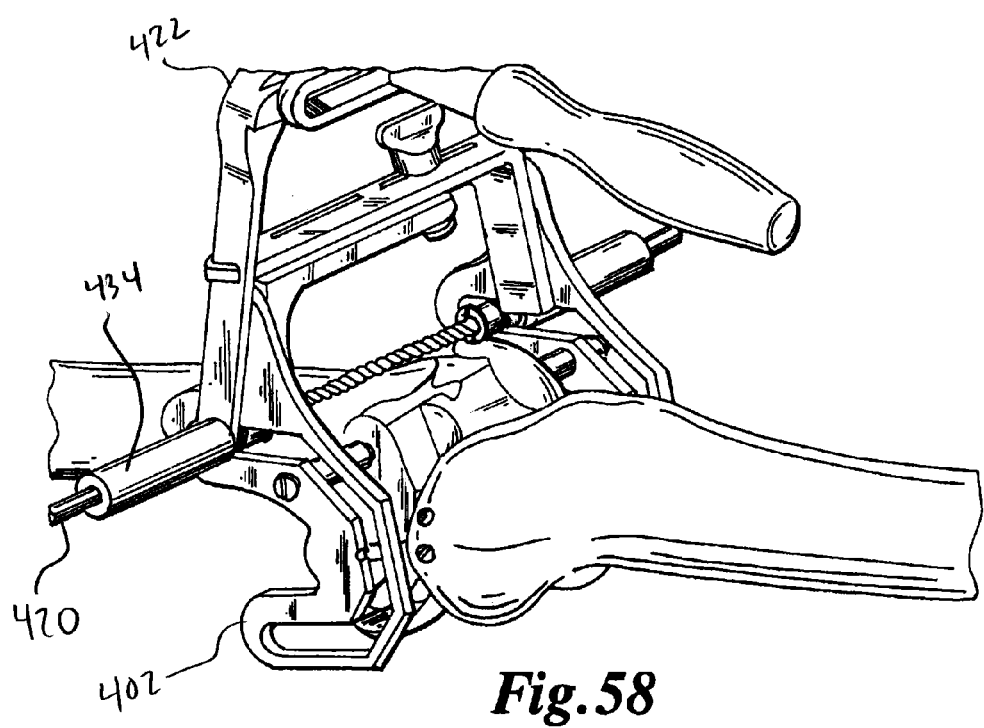
Figure 64:
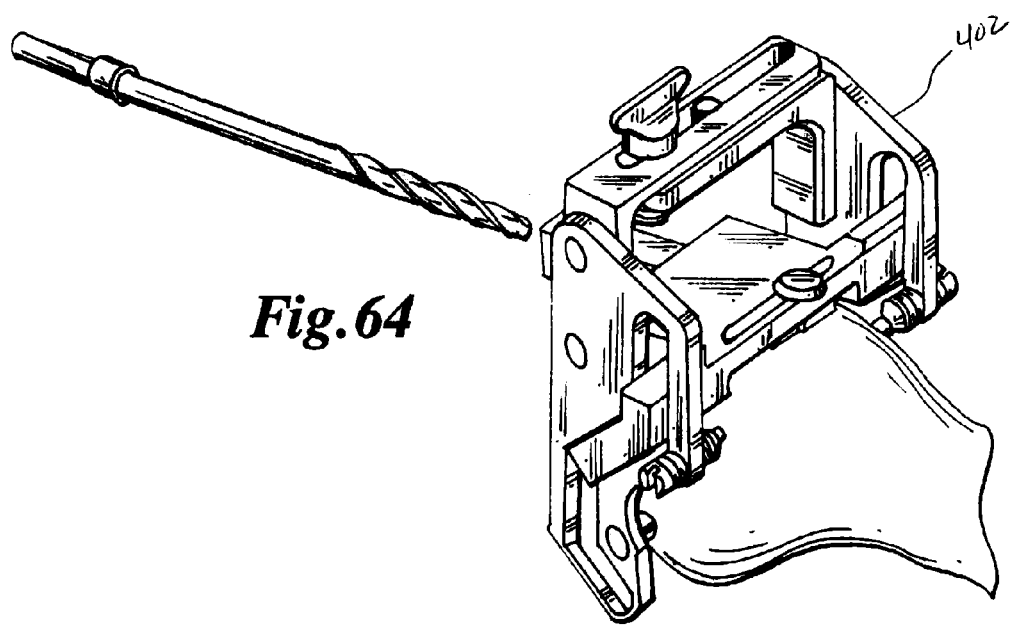
Figure 65:
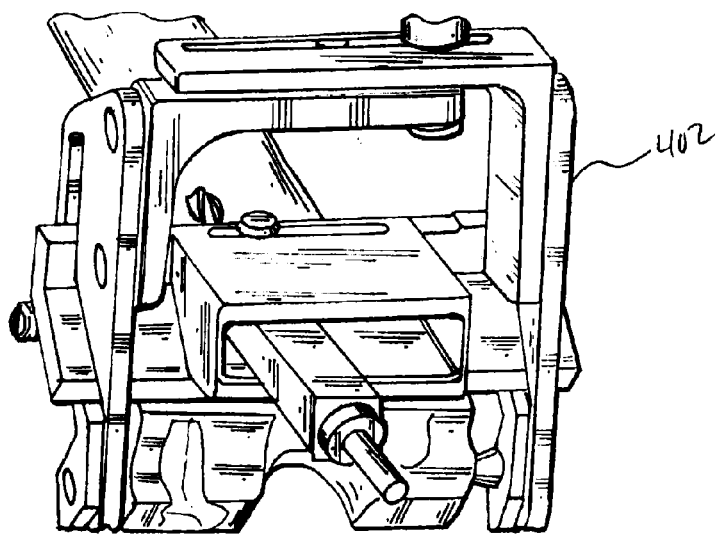
Figure 66:
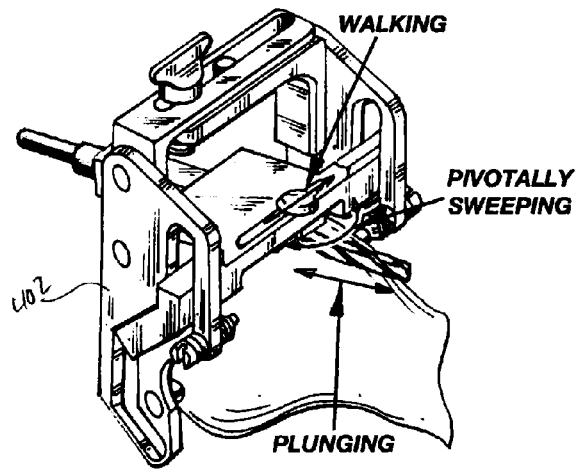
Figure 67:
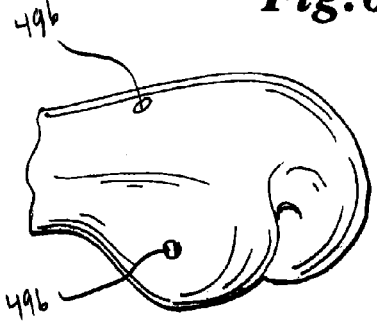

FIGS. 41 through 60 represent an embodiment of the present invention the soft tissue protection sleeves 428 and milling/drilling bit 420 management techniques that enable Triple Transcutaneous Transarticular TKA ("TTTKA" or "Triple TKA" or "T Cubed" or "$T^3$" Procedures). The soft tissue protection sleeves 428 shown, for example, in FIGS. 42 and 43. One clinical application calling for the benefits of this feature would be where a PBR cutting guide 402, as generally shown in FIG. 35 is positioned completely outside of the wound with the exception of fixation features 426 which extend from the externally located guides through skin incisions and into holes or apertures created in bone. As shown in FIGS. 52 and 53, the cutting tool 420, in the case of the present invention a side cutting drill, is extended through the handle 422, the guide 402, the skin, fat, capsule, etc (soft tissue), across, across and in front of, through, or beneath the articular surfaces of the joint, and through the soft tissue, guide 402, and handle 422 on the opposing side of the bone. The soft tissue protection sleeves 428 may be extended through the soft tissue and into contact with the sides of the bone. The retaining lip 430 can be used to maintain the sleeves 428 in contact with the bone and are held there by the edges of the incision through the capsule during cutting. The springs 432 shown in FIG. 43 can further bias the sleeves 428 into contact with bone in a manner that would maintain that contact as the width of the bone changed along the cutting path of the resected surface.

One skilled in the art will note that the thicknesses for the soft tissue through which the sleeves 428 extend change significantly from patient to patient thus requiring the proportions of the sleeve 428, spring 432 and other components of the present embodiment of the invention to change accordingly. For example, in an obese patient, the fat layer through which the cutting tool 420 extends can be 5 inches thick per side or more. The diameter of the soft tissue protection sleeve 428 can be significantly reduced with respect to what is shown as the side cutting drill diameter is reduced, thus requiring a smaller capsular or other soft tissue incision or 'stab wound'.

In operation, the handle 422 is manipulated to traverse the cutting path 404 of the cutting guide 402 while the tibia is swung through a range of motion about the femur as shown in comparing FIGS. 54 through 60. This particular principal of operation takes advantage of the fact that the capsule, the patella, and to a lesser or greater extent the skin, moves with the tibia as it moves through a range of motion with respect to the femur. Thus, a small, perhaps 4 mm to 10 mm long stab wound through skin to the medial side of the posterior femoral condyles (roughly in line with the axis of the pilot drill shown in FIG. 51) with the knee bent in flexion, and then looked at the side of the femur (through the portal created by the stab wound) while moving the tibia through a range of motion, the side of the femur would be observed to be passing by/through the portal. In order to complete all of the resected surfaces on the femur necessary to fix a standard femoral prosthesis, it may be necessary in one embodiment to make two passes with the side cutting drill 420 sweeping about the femur with the tibia as represented in FIGS. 54 through 60.

Figure 68:
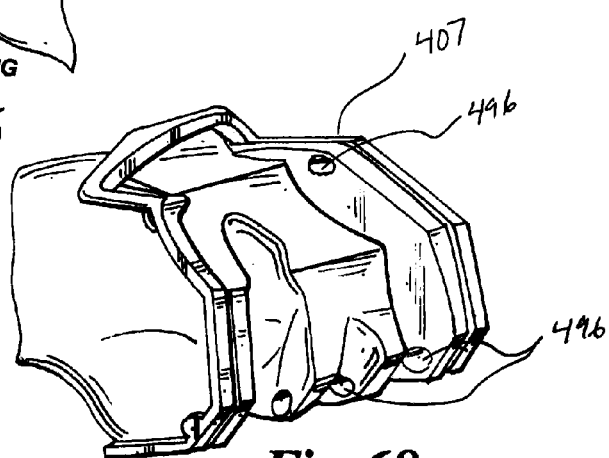

FIGS. 44 through 51 represent an embodiment of the present invention for use in creating pilot holes allowing for introduction of a side cutting drill or other cutting tool in Triple TKA or Unicondylar or Bicondylar procedures. Of particular interest, the pilot drill 421 is designed to eliminate or mitigate any deviations of the drill from its intended location and orientation as it is guided to create portals in living bone. Standard drills tend to follow the path of least resistance into and through bone often resulting in either poor drill placement, and thereby poor cutting guide 402 placement, or improperly located and oriented portals or apertures for fixation of a cutting guide resulting in poor cutting guide placement. As shown in FIG. 44, the pilot drill 421 possesses cutting teeth 423 that are very aggressive in side cutting. This is critical in that it prevents deflection of the cutting tool when it contacts tissue of varying material properties. This area of very aggressive side cutting teeth 423 is relatively short, and is followed by a longer smooth portion 425 of the shaft of the drill 421 which is designed to be incapable of cutting bone, but may beneficially include smooth flutes 427 allowing for removal of chips during the cutting process. A pilot drill 421 of this kind, optionally used in conjunction with the Surg Nav Drill Guide 190 of FIGS. 8 through 11, would be outstanding for use in creating the apertures in bone desired for positioning any number of cutting guides. Specifically, the pilot drill 421 may provide sufficient accuracy and precision of aperture 496 creation to allow for drilling all the way through or across a bone to which a cutting guide 407 will be attached to bone sides of the aperture 496 as shown in FIG. 68, where the cancellous bone within the cortical shell is not shown for the sake of clarity.

Figure 51:
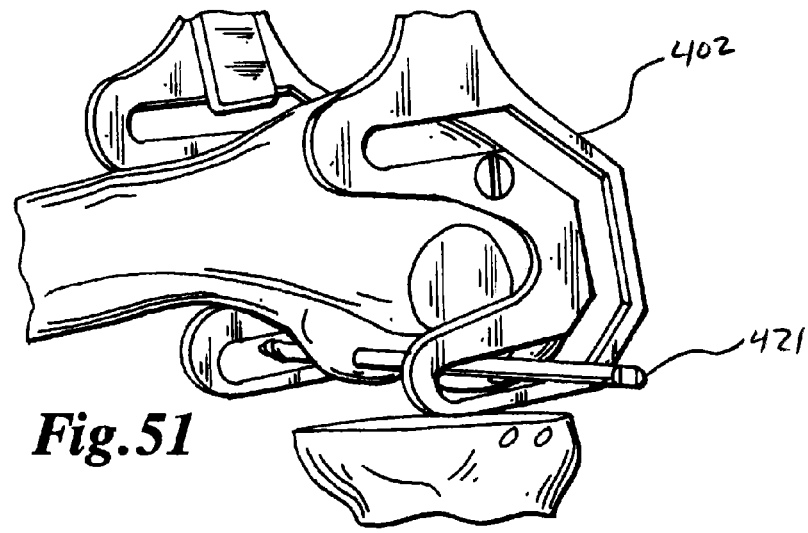

In use with the embodiment of the present invention, with the soft tissue protection sleeves 428 of the milling handle 422 in contact with a bone surface, the pilot drill 421 would be plunged through the bushings 434 of the milling handle 422 and across the joint, as shown in FIGS. 45 through 51. FIG. 51 represents the pilot drill 421 having been plunged entirely across the joint, but with the milling handle not shown for the sake of clarity. Thus, a portal has been created across the entirety of the joint for subsequent insertion of the side cutting drill 420 shown in FIGS. 52 and 53, or any other cutting tool. It should be noted that in embodiments adapted for use in Unicondylar knee replacement, it would only be necessary to create the portal in one side of the joint for extension of the cutting tool 420 across only a single condyle (as is seen in comparing FIGS. 78 and 80). An alternative embodiment and method of the milling handle 422 of the present invention represented in FIG. 54 would be to extend the side cutting drill 420, or other cutting tool, through a soft tissue portal on one side of the joint, across the entirety of the bone surfaces to be resected or cut, but not extend the tool through the soft tissue on the far side of the joint. As control of the side cutting drill by the milling handle 422 is very robust, even when it supports only one spindle of the side cutting drill, accurate and precise preparation of the distal femur can be performed without necessitating a second soft tissue portal, and the soft tissue trauma associated with it, no matter how minor, on the far side of the joint.

Figure 69:
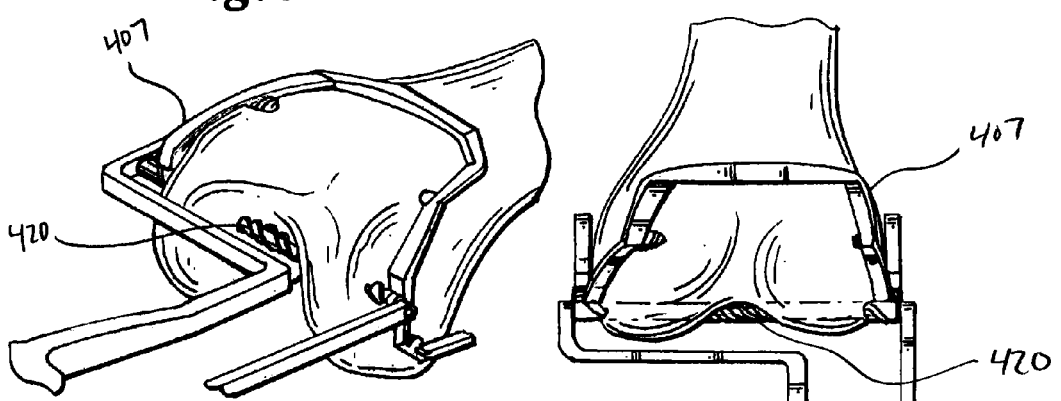
Figure 70:
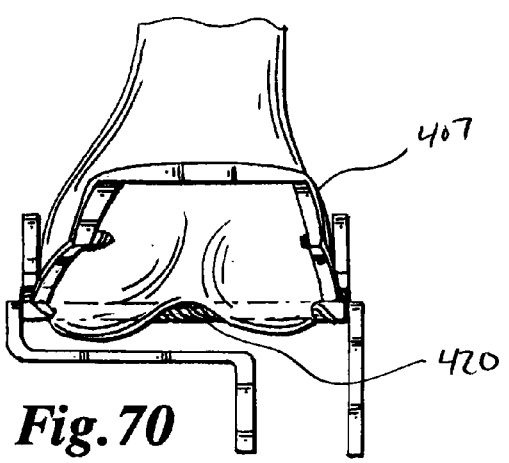
Figure 71:
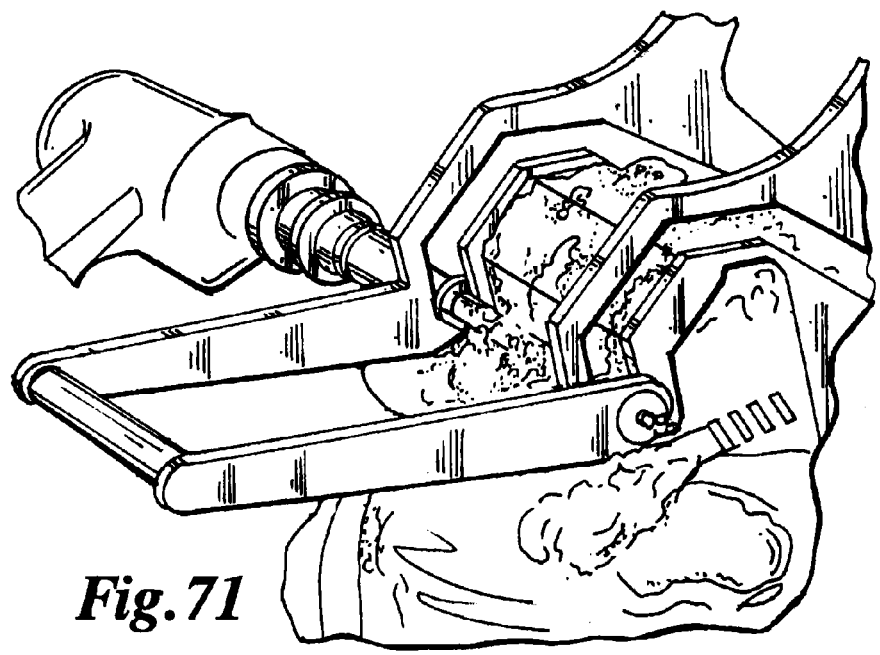
Figure 72:
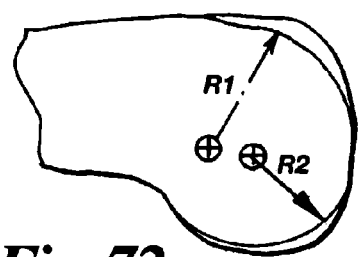
Figure 73:
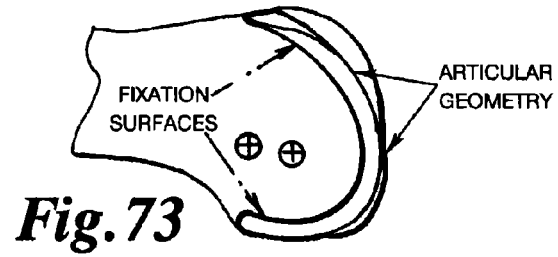
Figure 74:
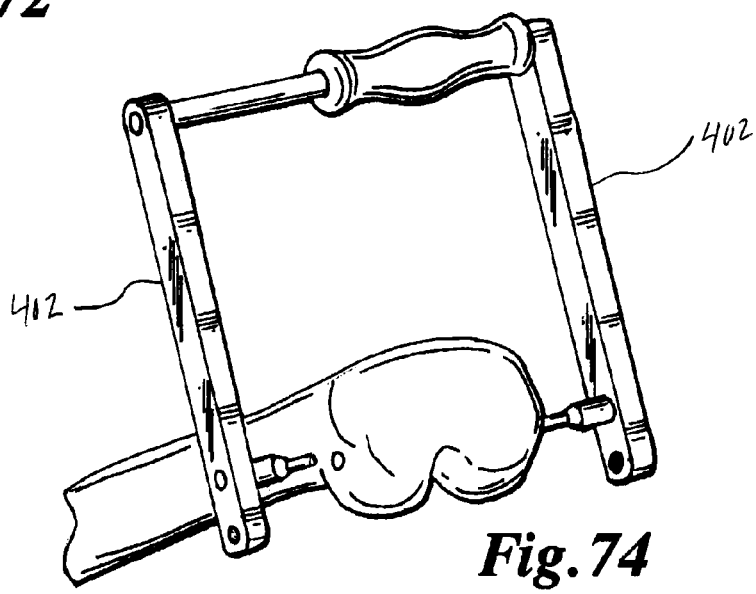
Figure 75:
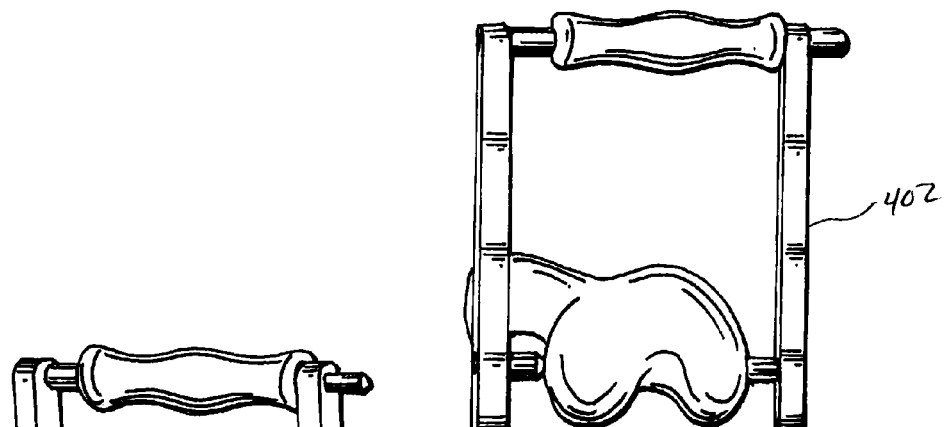
Figure 76:
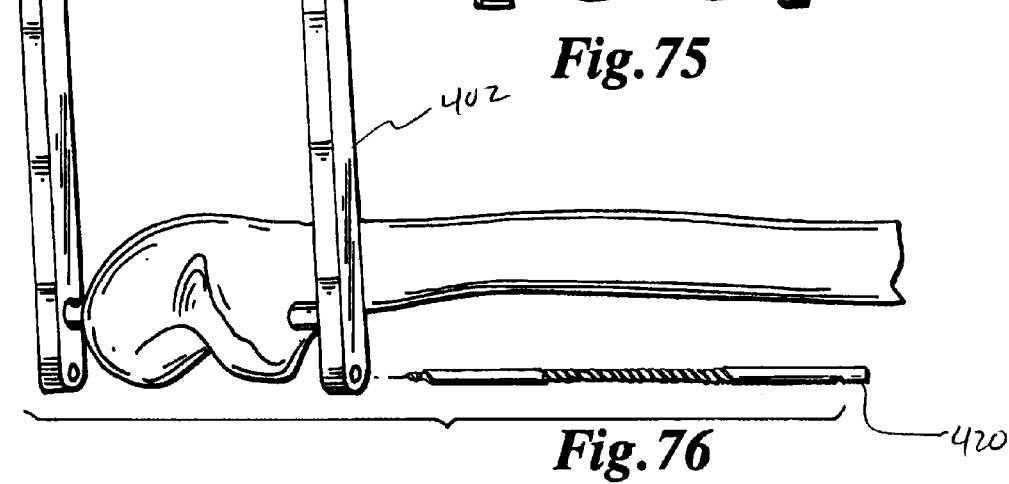
Figure 77:
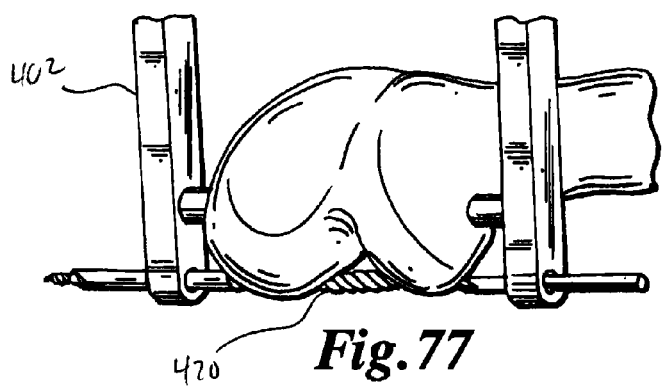
Figure 90:
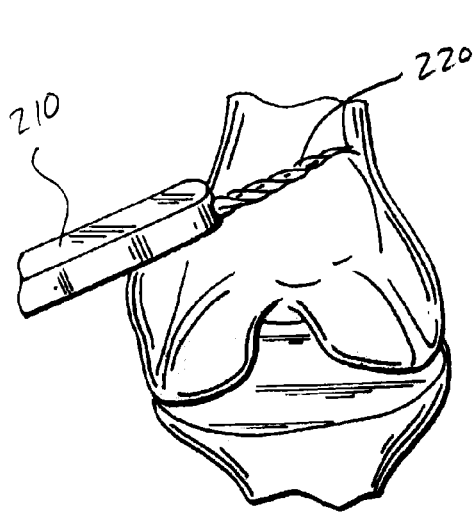
Figure 91:
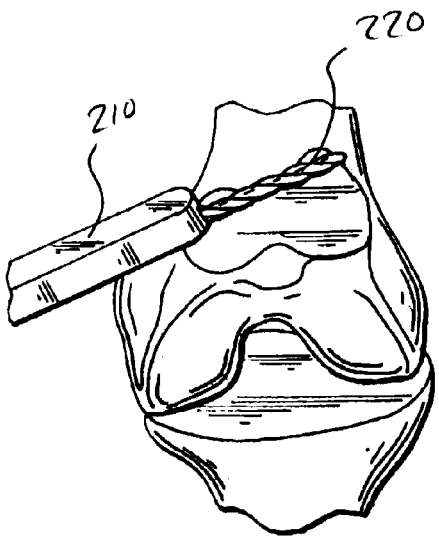
Figure 92:
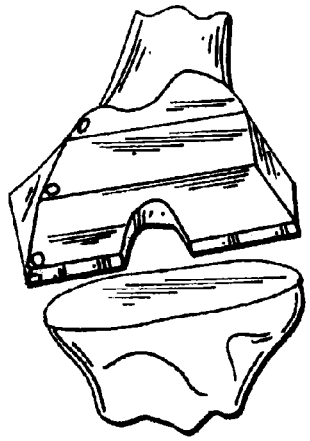
Figure 93:

Alternatively, a hybrid embodiment of externally and internally located guide surfaces would allow for high precision, high accuracy cutting without necessitating the creation of soft tissue portals for insertion of the cutting tool 420. This embodiment of the present invention can be attained by positioning one PBR cutting guide surface(s) in the wound (perhaps looking like the medial guide surface of the cutting guide 407 shown in FIGS. 68 through 70) and interconnecting it with an externally located PBR cutting guide surface(s) (for example, looking like the laterally located plate in FIG. 60). This would allow for single spindle guidance of the side cutting drill or other cutting tool in a very robust manner, while minimizing the trauma to soft tissues necessary to implement these embodiments. Furthermore, the use of these single spindle embodiments lend themselves to easy manipulation of the cutting tool in pivotally sweeping (see FIG. 85) a cut surface while manipulating the cutting tool axially with respect to the milling handle. Thus the anterior chamfer cut, distal cut, and posterior cut could be completed by sweeping the cutting tool along the cutting path of the cut surface, and the anterior and/or posterior cuts could be completed by pivotally sweeping the cutting tool as mentioned above while maintaining the stability inherent in guiding the milling handle on guide surfaces on opposing sides of the cut being created. This is beneficial in that the internally located guide surfaces could be truncated or shortened significantly allowing for both easier insertion into the surgical exposure and reduction in the exposure necessary to accommodate the embodiments in clinical use.

FIGS. 5 through 11

Figure 5:
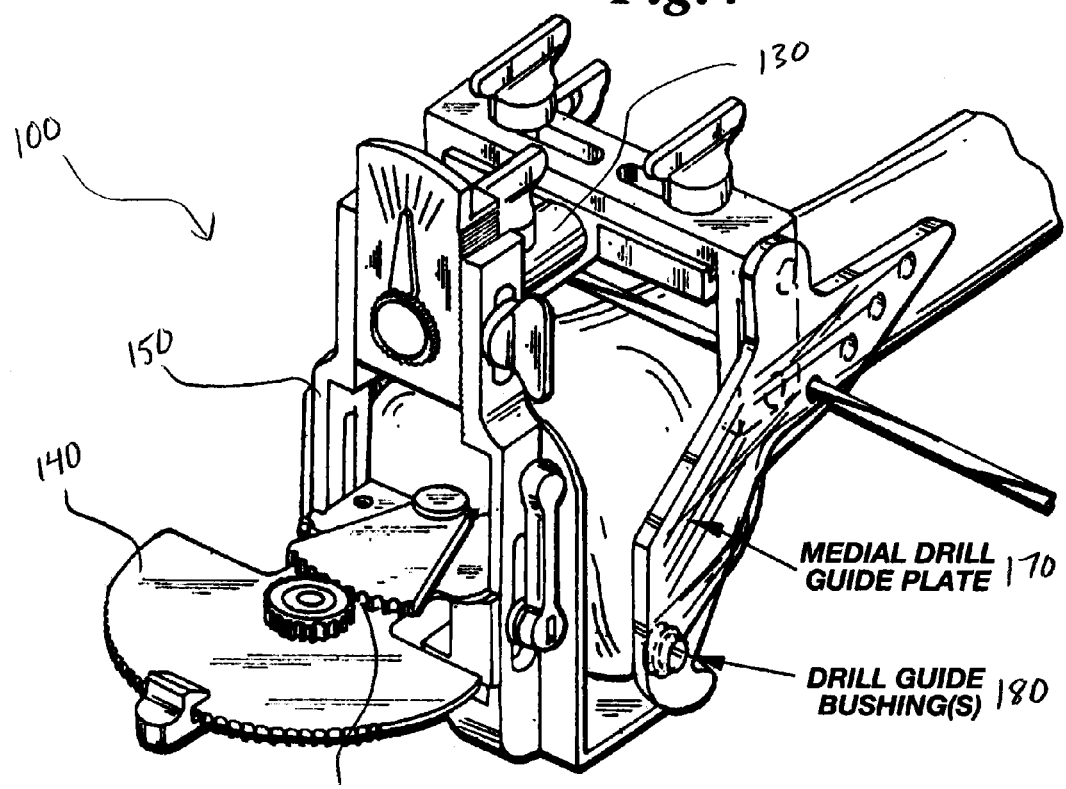
FIGS. 5-98, 111, 119, and 125-127 show various depictions of embodiments and methods in accordance with alternate embodiments of the present invention.

FIGS. 5 through 11 concentrate on alignment guide and/or drill guide techniques. FIG. 5 shows a manually operated alignment guide 100 suitable for use with surgical exposures similar to that shown in FIG. 2 (it should be noted that surgical navigation sensors could be used to assist in determining final drill guide location and orientation). FIGS. 6 and 7 show an improvement upon the embodiment shown in FIG. 5 for enabling manual alignment guide use in less invasive incisions by providing soft tissue accommodating contours or reliefs 110. In other words, for a medial parapatellar incision, the alignment guide 100 is configured to allow for appropriate contact and referencing of the distal and posterior femoral condyles, the IM canal (when not relying on an extramedullary reference or inference of the mechanical axis) or IM Rod 120, the anterior cortex or anterior runout point of a given or proposed implant size (via a stylus not shown), and the epicondylar axis via palpitation or visual reference while the patellar tendon, patella, and/or quadriceps tendon is draped over the lateral side (right side as shown in the figures) of the alignment guide 100 allowing insertion of the guide when the patella is neither everted not fully dislocated as in conventional techniques. It should be noted that initial alignment indicated by reference of the distal femur may be further adjusted in all six degrees of freedom as a fine tuning for final cut location and orientation. This simply calls for the inclusion of additional adjustment of the location and orientation of the crossbar mechanism 130 and/or rotational alignment arm 140, with respect to the initial reference provide for by contact between the body 150 of the guide 100 and the bone (optionally including the IM Rod 120), in flexion-extension angulation, varus-valgus angulation (rotational angulation and Anterior-Posterior location are already shown), mediolateral location (represented in this embodiment of the current invention by the cross bar mechanism 130 in FIG. 5 where drill guide mediolateral location is shown as being independently and infinitely adjustable), and proximal-distal location (as shown in FIGS. 5, 6, and 7—it should be noted that this adjustment might be best embodied in an infinitely adjustable slide as opposed to the incrementally adjustable slide 160 shown, and that simple marking would be present indicating the relative movement of the slide with respect to the body). It may be desirable to only utilize only a medial drill guide plate 170 with multiple drill guide bushings 180 to create holes extending partially or completely across the femur depending upon the manner in which the guides are to be connected to the femur.

Figure 9:
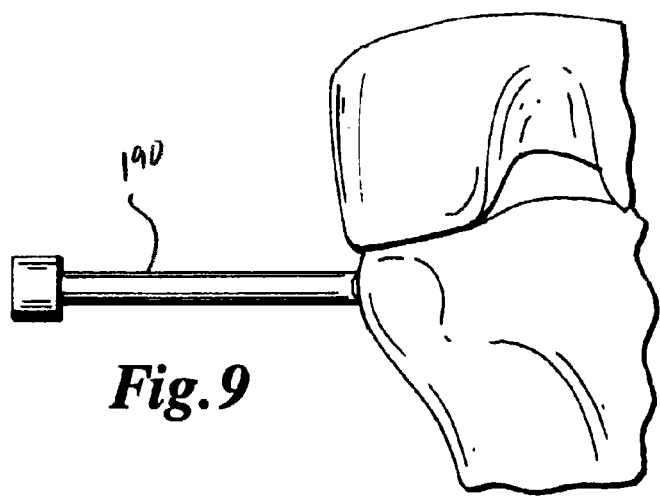
Figure 10:
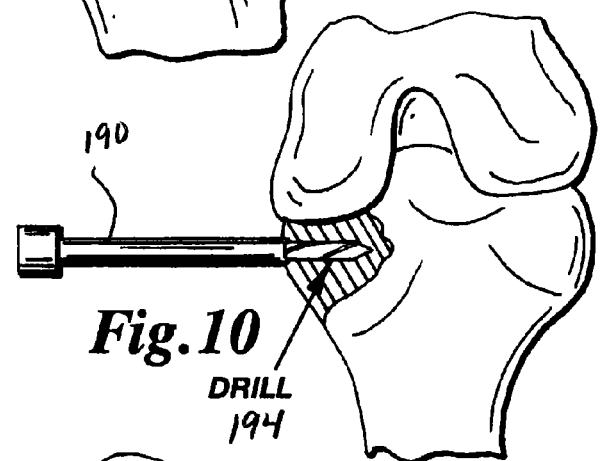
Figure 11:
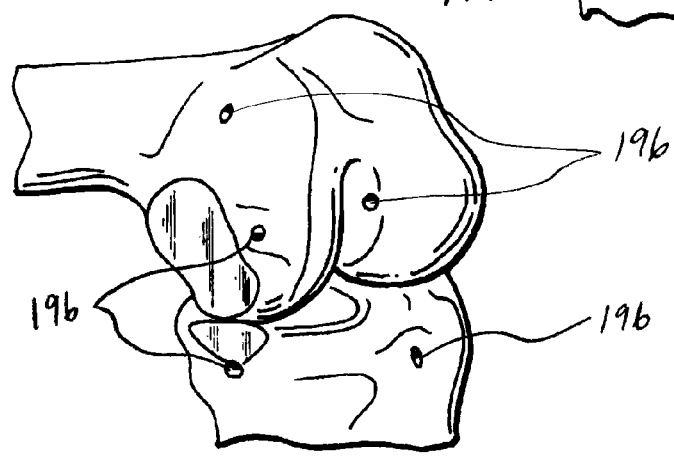

FIGS. 8, 9, and 10 show an alternative alignment/drill guide embodiment of the present invention wherein a cannulated surgically navigated handle/drill guide 190 is used to create fixation apertures in the bone for direct or indirect fixation of a cutting guide. As shown in FIG. 8, it may be advantageous to include tines 192 for penetrating the bone to obtain initial stabilization of the handle in the location and orientation indicated by the surgical navigation system ("Surg Nav"—this term shall be used interchangeably with Computer Aided Surgical System or Image Guided Surgical System throughout this disclosure) prior to extending the drill 194, represented in FIG. 10, into the bone to create the aperture. It should be noted that the aperture 196, or hole, thus created could be blind or extended to a specific depth, or optionally extended entirely through the bone and out the furthest side of the bone. Importantly, this process could be utilized transcutaneously through a small stab wound (perhaps 4 mm in length) through the skin to the bone surface, or through a preformed incision through which other instrumentation of the present invention or other devices may be introduced during a procedure. Further, although only one cannulation is shown, a single handle may desirably contain multiple cannulations, some or all of which could be adjustably extended into contact with the bone to reduce any wandering of the drill 194 contacting oblique bone surfaces and improve the precision and accuracy of aperture creation (thus allowing for the creation of apertures 196 in the medial side of the femur, represented in FIG. 11, with a single Surg Nav Handle—Also, the apertures 196 may be configured such that the femoral and tibial apertures 196 shown in FIG. 11 are all created using a single positioning step for the handle). As represented in FIG. 9, there is very little distance over which the drill 194 is cantilevered between its guidance within the cannulations and its point of initial contact with the outer surface of the bone. This aspect of this embodiment of the current invention is critical in preserving the potential accuracy of Surg Nav systems, i.e.; the navigation system (the computer and the sensors) may be capable of determining appropriate location and orientation to ±0.1 mm and ±0.5 degrees, but if the location and/orientation of the aperture created represents some path of least resistance in bone which is followed by the drill 194, the resultant location and orientation of cut surfaces, and thereby the location and orientation of the prosthesis attached thereto, will likely be seriously in error.

It should also be noted that the methods described herein are applicable to the methods demonstrated in Provisional Patent Application Ser. No. 60/536,320, entitled "Methods and Apparatus for Pinplasty Bone Resection" and Ser. No. 60/xxx,xxx, entitled "Methods and Apparatus for Wireplasty Bone Resection," the disclosures of each of which are hereby incorporated by reference.

It should also be noted that another embodiment of the present invention, represented in FIGS. 88-92, benefits from the apparatus and principles of operation outlined above. As shown in FIG. 88, an aperture 202 and a plane 204 are created in bone which actually act as the cutting guide 200 in controlling the location and orientation of the cutting tool 220 within a specific plane during the creation of a cut surface. In this embodiment of the present invention, the cannulated drill guide will, in either manual or Surg Nav techniques, be used to guide a forstner style drill bit (the 'guide surface' 200 shown in FIG. 88 could have been created by a modified drill with a leading section 15 mm long by 4 mm in diameter, responsible for the pivot aperture 202, and a 10 mm diameter following section which was about 10 mm long, responsible for the pivot reference surface 204) to create a larger diameter cylindrical aperture the bottom of which would define a pivot reference surface 204 parallel to the cut surface to be created, and a smaller diameter cylindrical aperture to form a pivot aperture 202 for maintaining the body of the bushing 210 shown in FIGS. 88-91 in the proper location and orientation while cutting. Importantly, the technique outlined above is beneficially applied to tibial resection or any other planar or curvilinear resection technique as well.

FIGS. 12 through 34

FIGS. 12-34 disclose embodiments of the present invention for creating planar and/or curvilinear resection surfaces on or in the proximal tibial and other bones and embodiments of the present invention for prosthetic implants.

FIGS. 12-15 represents an embodiment of the present invention for cutting guides and cutting tools which substantially comprises a guide 200 with guide pivot aperture(s) 202 and a guide pivot reference surface(s) 204 for mating with a bushing 210 controlling a cutting tool 220, wherein the bushing 210 possess a bushing reference plane 212 (which mates with the pivot reference surface(s) 204 of the guide 200), a bushing pivot pin 214, best represented in FIG. 88 (which mates with the guide pivot aperture(s) 202 of the guide 200), and a cannulation 216 for articulated and/or axial guidance of the cutting tool 220.

There are a number of optional features that are highly desirable depending on the preferred method of use utilized for these embodiments of the present invention. The soft tissue protection tip 222 of the cutting tool 220 and the integral soft tissue retractor feature 218 of the bushing body 210 are two principal examples represented in FIG. 20. The soft tissue protection tip 222 can be integrally formed as a part of the cutting tool 220 during its manufacture, be a separate component attached to it, and may, in one preferred embodiment, be free to rotate with respect to the cutting tool 220 (which would be useful in preventing rotating bearing contact between the tip and soft tissue). The integral soft tissue protector 218 in beneficial in preventing or mitigating contact between soft tissue near the area where the cutting tool 220 enters, cuts, and exits the wound (in other words, to the right and left of the bushing body 210 shown in FIG. 13). If you picture the incision as being a window into the joint which is somewhat elastically moveable from side to side, the integral soft tissue retractor 218 would act to shift that window to mitigate or prevent contact between the soft tissue (specifically the patella tendon, medial or lateral collateral ligaments, the capsule, skin, fat, etc.) and the cutting surfaces of the cutting tool 220.

In operation, the guide is properly positioned with respect to the proximal tibia and the cut to be created thereon and robustly fixed with respect to the tibia or directly to the tibia. This can be accomplished by manual alignment means outlined in U.S. Pat. No. 5,643,272 for manually positioning guides then fixing them in place, or use the '272 apparatus and methods to create the fixation apertures 196 shown in FIG. 11 or 12, or use the Surg Nav techniques described herein as shown or in conjunction with the methods described in the '272 patent. The bushing body is then engaged with the guide. Three primary methods of initiating cutting of the proximal tibia are preferred. The first, or 'Tangent Method', is initiated by extending the side cutting drill through the bushing body cannulation and into contact with a side of the tibia and then sliding the optional non cutting tip along the face of the bone until the cutting surfaces of the cutting tool were first in contact with the side of the bone. At this point, the cutter could be actuated to begin cutting the boney tissue to create the cut surface. As the non-cutting tip cannot cut bone, its edges would remain at all times immediately beyond and adjacent to the boundary of the cut surface being created. The diameter or size may be greater or less than the diameter or size of cutting surfaces of the cutting tool. Note that although the embodiment of the cutting tool shown is a side cutting drill, a modified rat tail rasp driven by a reciprocating driver could also work well—any cutting tool capable of cutting in a direction orthogonal to its long axis is considered to be within the scope of the present invention.

Figure 15:
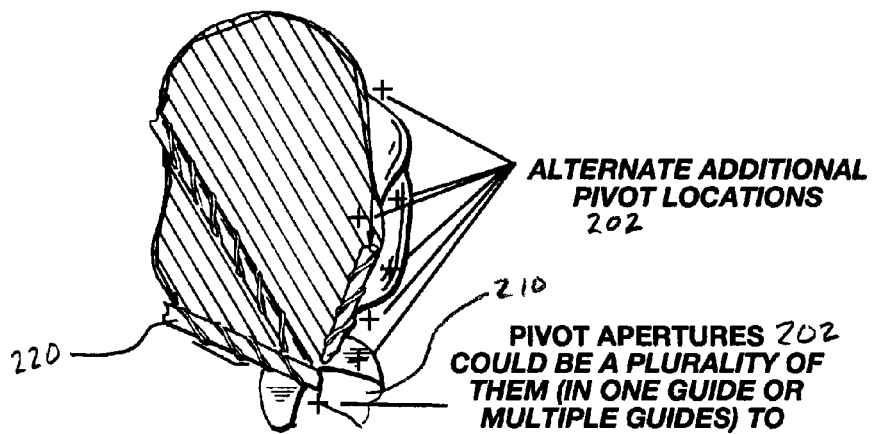

As best represented in FIG. 15, the entirety of the resected surface may be prepared in this manner. The second primary method is the 'Plunge Then Sweep' method. In this method, the cutting tool or optionally a pilot drill would be plunged completely or partially across the surface to be cut. Then the cutting tool could be swept back and forth in clockwise and counter-clockwise directions while being axially manipulated to complete the cuts. The third primary method is the 'Chop Then Sweep' method represented in comparing FIGS. 88 and 89. In this method, the cutting surfaces of the cutting tool are positioned over and at least partially across the uncut bone, then chopped down into it by manipulating the bushing. In other words, the bushing pivot pin is engaged with the pivot aperture with the cutting tool positioned over the bone which positions the bushing reference surface at a distance above the pivot reference surface, then the bushing is moved downward along the axis of the bushing pivot pin while the cutting tool is under power until the cutting tool reaches the cut surface to be created (if the cutting tool is a side cutting drill, the cutting surfaces would be tangent to the desired cut surface at that time). The bushing is then manipulated as described hereinabove to complete the cuts. Importantly, the pivot reference surface and pivot aperture could be slidably mounted to a base component fixed with respect to the tibia so that the surgeon may manipulate the bushing body to simultaneously create the cut and move the pivot aperture with respect to the tibia. This embodiment will enable the surgeon to easily compensate for any soft tissue condition encountered clinically while preserving the benefits of the present invention. Methods combining the aforementioned primary methods are considered to be within the scope the present invention. Importantly, most standard or prior art tibial resection cutting guides may be simply modified to include the pivot apertures described herein.

Figure 16:
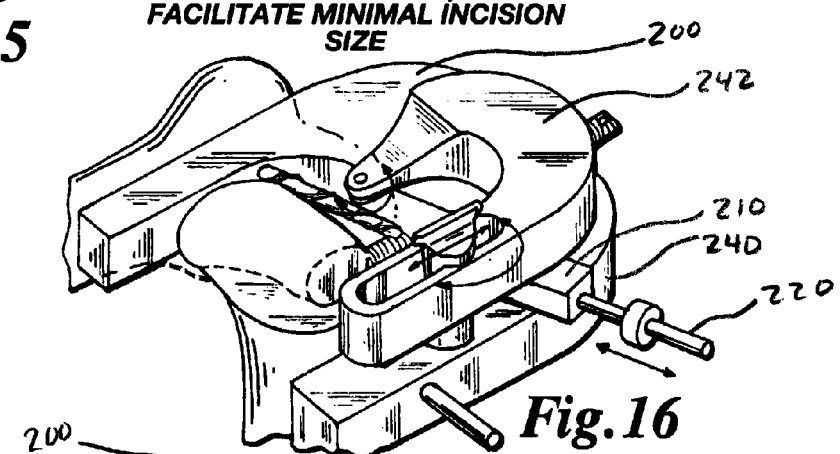
Figure 17:
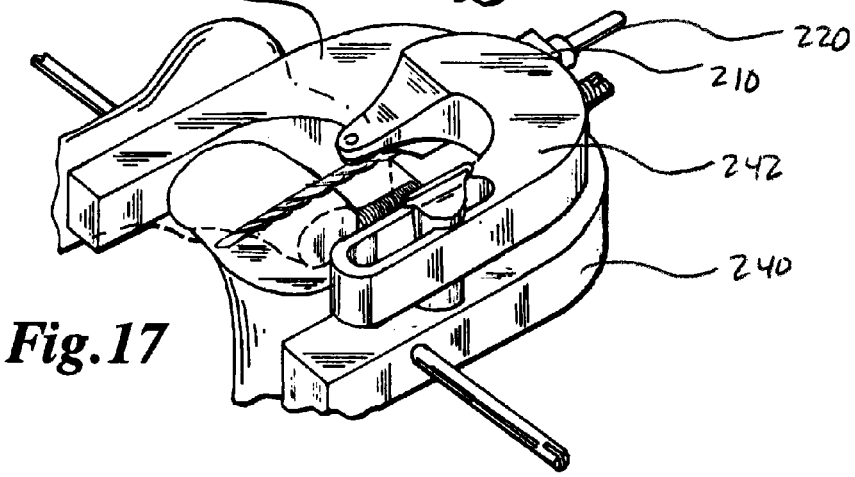
Figure 18:
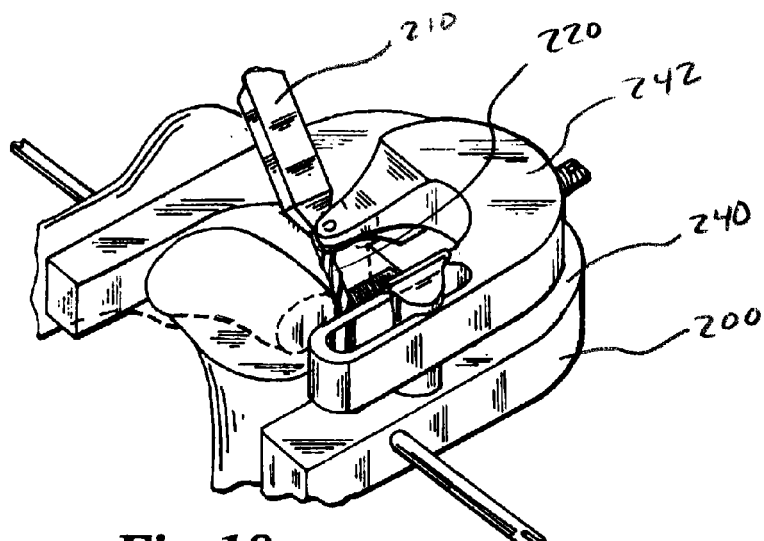
Figure 19:
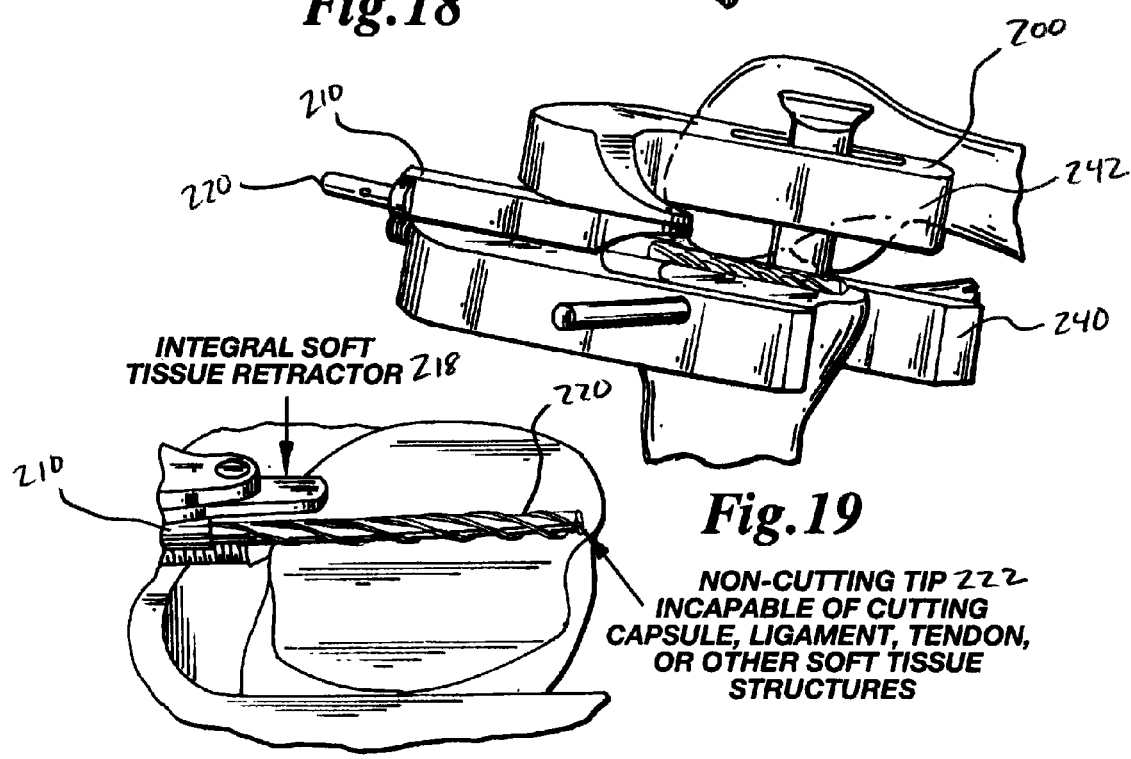
Figure 20:
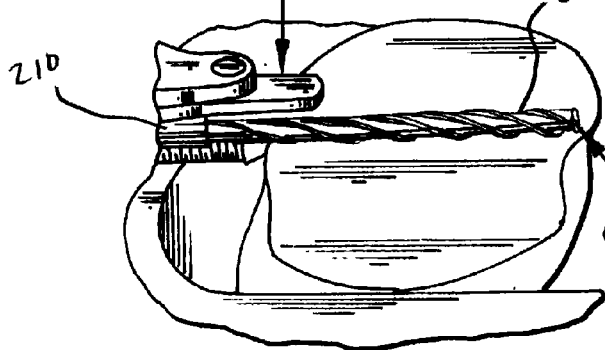
Figure 21:
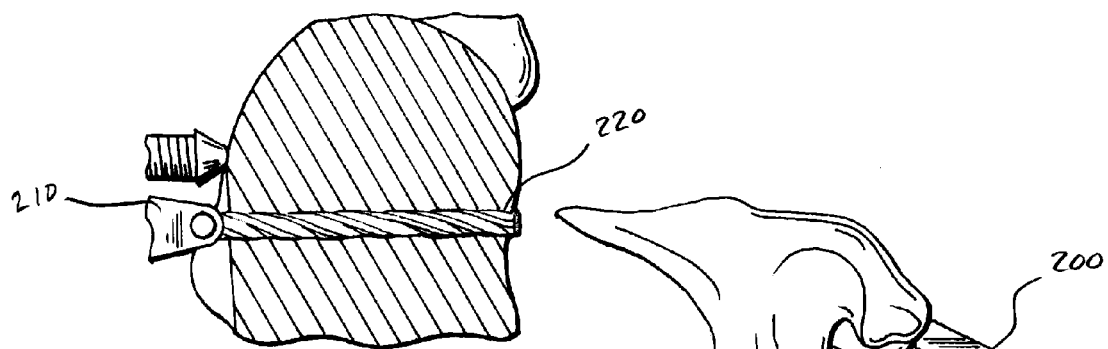
Figure 22:
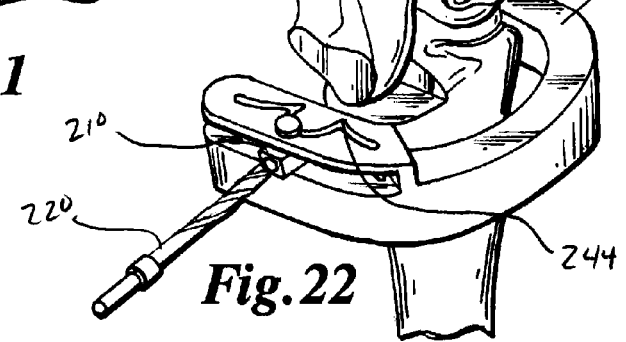
Figure 23:
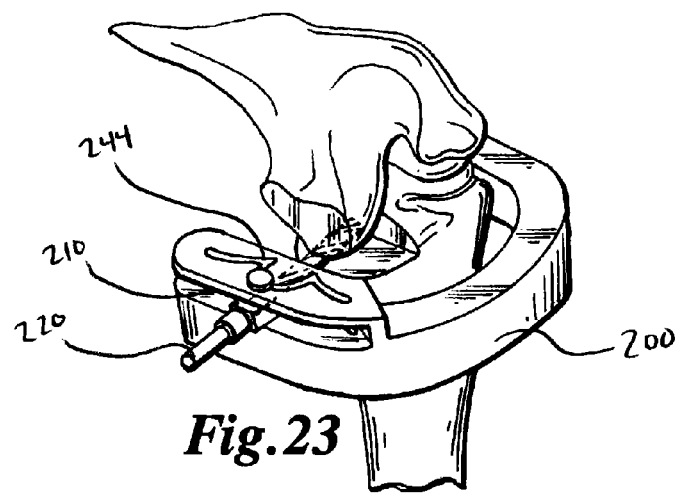
Figure 24:
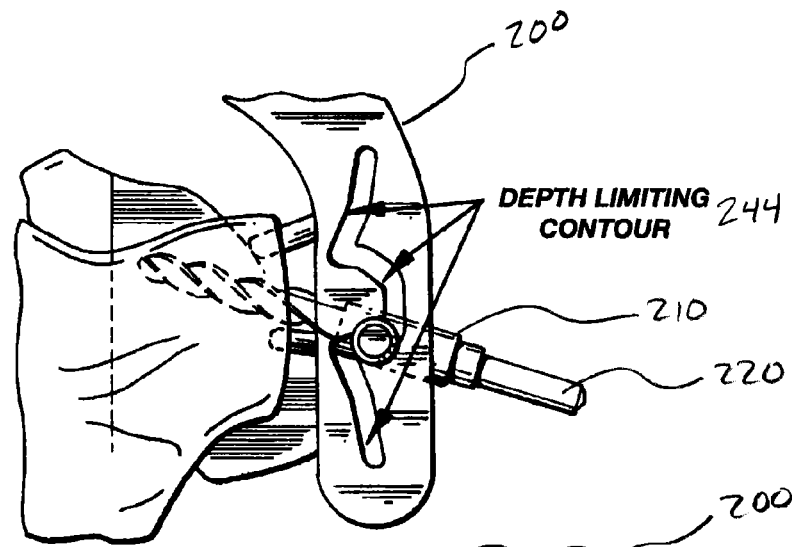
Figure 25:
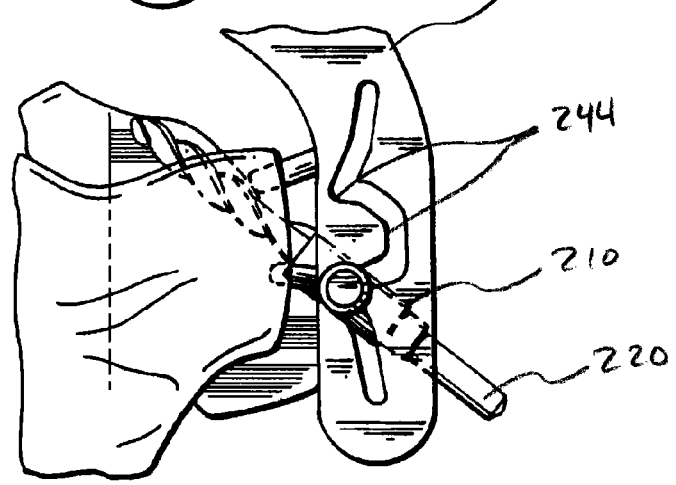
Figure 26:
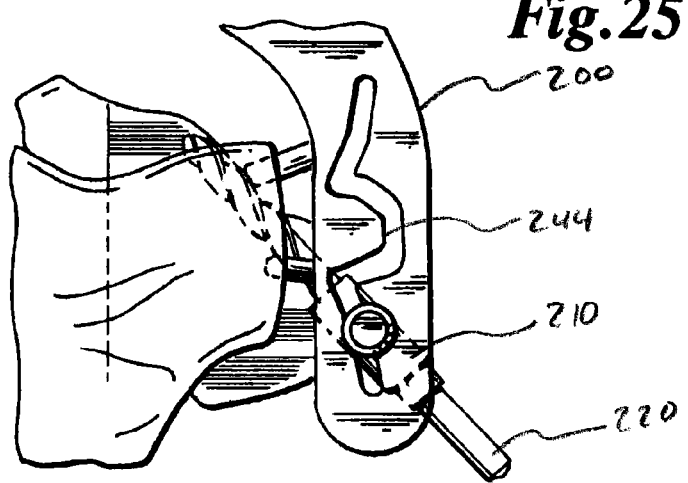

FIGS. 16 through 21 describe another embodiment 200 of the present invention. As shown in FIG. 16, this embodiment includes a Base 240 and a Rotational/Translational Pivot Arm 242 coacting to allow for infinite manipulation of the bushing 210 pivot pin 214 location within a desired plane during the process of removing material from the proximal tibia or other bone. Movement of the Rotational/Translational Pivot Arm 242 in both rotational and translational degrees of freedom within a desired plane allows for any combination of rotational and translational movement of the axis of the bushing pivot pin 214 within its desired plane. In other words, this embodiment of the present invention allows for infinite and continuous adjustability of cutting tool 220 location and orientation with respect to the bone or bones being cut while providing for accurate and precise cut surface creation.

FIGS. 22 through 28 represent another embodiment 200 of the present invention whose principal of operation are similar to previous embodiments, with the exception of including a depth limiting contour 244 which acts as either a definitive limitation for cutting tool 220 depth or as a general guideline for a surgeon to follow as the patient's clinical presentation and the surgeon's judgment dictate. Although the embodiment shown is directed toward Unicondylar tibial preparation, it should be noted the any clinical application where such definitive or guideline type depth guidance is desirable.

Figure 30:
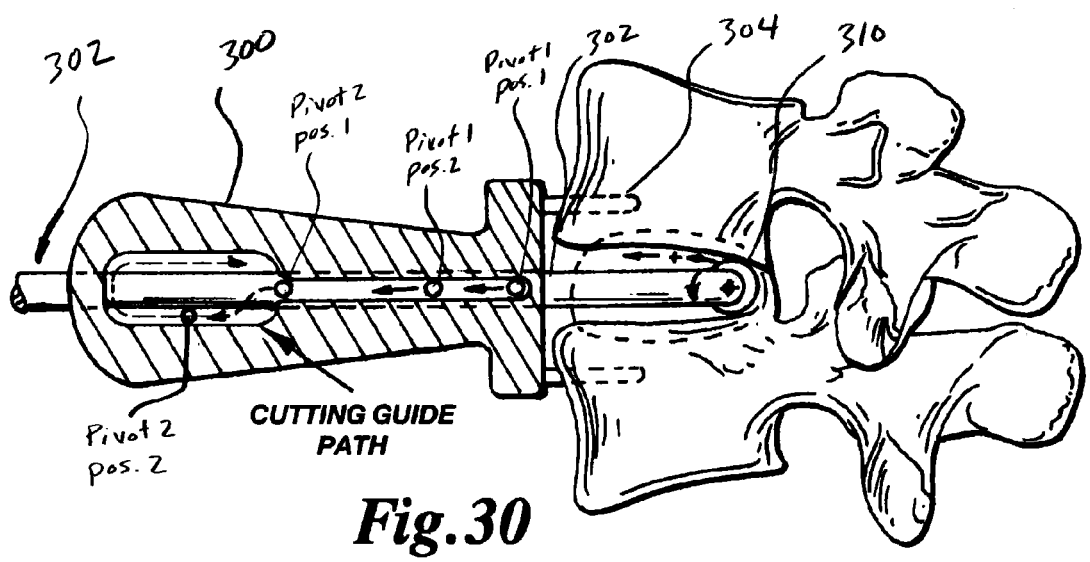
Figure 31:
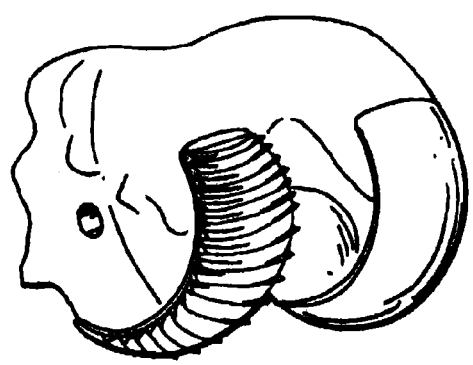
Figure 32:
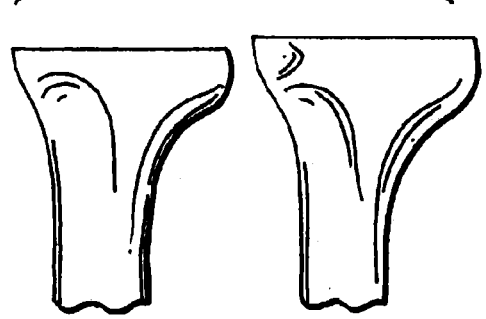
Figure 33:
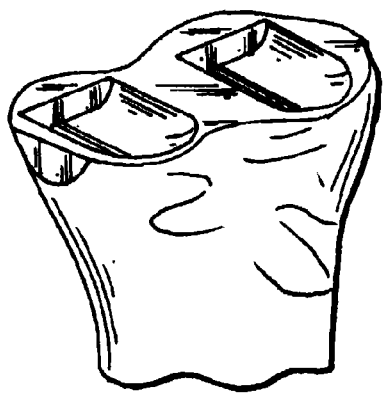
Figure 34:
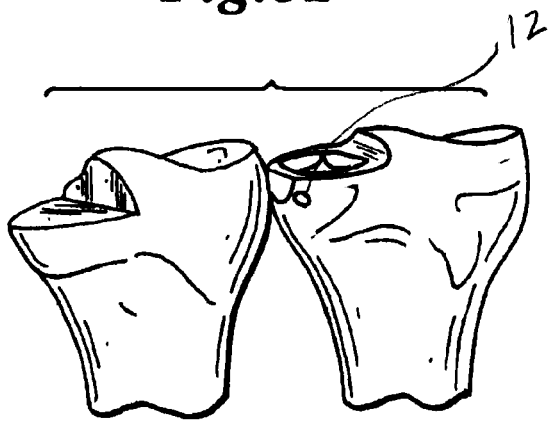

FIGS. 29 and 30 show an embodiment 300 of the present invention directed toward endplate preparation in spinal reconstruction where the endplates are prepared to receive a prosthetic implant. Guide 300 includes a milling handle 302 to which the cutting tool 310 attaches. It is interesting to note that the profile of the cutting path 312 of the guide 300 represented in FIG. 30, in this embodiment, is geometrically identical to the cutting path of the resected surface created by the passage of the cutting tool 310 shown. This could be very helpful in clinical application where such a device where inserted into a wound such that, while the surgeon could not visually observe the cutting tool 310 while it removes boney material, he could, by way of the guide geometry, observe where the cutting is with respect to the bone being cut by looking at the position (represented by "POS 1" and "POS 2") of 'Pivot 2', represented in FIG. 30, with respect to its location in contact with the guide as it traverses the cutting path of the cutting guide. This embodiment is also highly applicable to tibial resection and could allow for cut geometries that are anatomically curved in both AP and ML profiles to both preserve bone and improve fixation quality and load transfer characteristics between the implant and the bone by converting the shear component load of conventional planar tibial components into compressive loads via geometrically normal or transverse abutment of bone and implant surfaces in the direction of A-P and/or M-L and/or torsional shear loading. An implant design embodying fixation geometries for mating with such cut surfaces is highly desirable. In one embodiment of such a tibial prosthesis design, the fixation surfaces would be intended to mate, directly or indirectly, with cut surfaces represented in FIGS. 33 and/or 34 (the tibia in the right side of the FIG. 34). In essence, the tibial implant would possess a planar or gently curvilinear 'rim' for contacting the 'cortical skim cut' surface (represented in FIG. 32), and convex fixation surfaces for direct or indirect fixation to the concave tibial cuts represented in FIGS. 33 and 34. Direct fixation to such surfaces could be achieved by high precision resection of both the cortical rim, for attachment of the rim of the tibial prosthesis, and the concave surface(s), for intimate apposition to the convex implant surfaces. Such fixation, specifically of the concave bone cuts to the convex implant surfaces, could be achieved by way of an interference fit between the cuts and the implant along one axis (for instance, a front to back—AP—axis or direction), or along two axes (for instance, AP and Side to Side—ML—axes), or circumferentially (in other words a bit like a pin of a given diameter being forced into a hole of a lesser diameter), or both circumferentially and along an axis at roughly a 90 degree angle or normal to the skim cut surface when viewed in one or two orthogonal planes (an "up and down axis" or superior-inferior or proximal distal direction). It should be noted that an interference fit in a roughly superior-inferior direction may call for a textured surface on the bottom most surface of the convex fixation surfaces presents a small surface area of contact at initial contact with the bottom of the concave cut to allow the implant to compact a reduced area of cancellous bone as the implant is impacted in a superior to inferior direction until it reaches its desired superior-inferior location and/or contact between the rim of the implant and the skim cut of the cortices. As compared to previous methods of achieving implant fixation, these embodiments of the present invention yield superior stability of implant fixation to bone to an extent reminiscent of the difference between riding a horse wearing a deeply dished saddle and riding a very sweaty horse bareback.

An alternative fixation paradigm allows for less intensive demands for the precision of the fit between concave tibial cuts and convex fixation surface. In essence, the concave surface may be 'excavated' in any desired manner (such as the Cutting Trials shown in FIG. 31 which cut the proximal tibia while the tibia is moved through at least a portion of its range of motion about the femur), and a morselized or granular osteobiological substance, perhaps tricalcium phosphate, HATCP, or other substances generally described as 'bone substitutes' or autograft or allograft cancellous or cortical bone (it would be very useful to use the bone which was removed from the tibia or other patient bone during the creation of the cut(s) in that it is readily available and completely avoids the issues of disease transmission or immune response), is then impacted into the concave surface using a 'form' to create a surface of impact material (referred to herein as the "Impacted Surface") of specific shape and location/orientation with respect to the cortical skim cut and/or the tibia or femur. This form is beneficially shaped in a manner related to the shape of the convex implant fixation surface shape so as to create a specific geometric relationship between the implant fixation surfaces and the Impacted Surface geometry. In one embodiment of the present invention, the fit between the implant and the Impacted Surface would be an interference fit or press fit. As properly impacted morselized cancellous bone is known to achieve stiffnesses (or modulus of elasticity) which approach as much as 80% of the stiffness of cortical bone in compression, robust intraoperative fixation may be achieved in this manner. In another embodiment, the fit would leave a significant gap, perhaps 0.2 mm to 4.0 mm in width, between portions or all of the convex fixation surfaces of the implant and the convex cut(s), into which bone cement or other substance would then be injected or impacted achieving interdigitation with both the surfaces of the prosthesis and the material of the Impacted Surface. This results in what could be described as composite interface of both biologically active and non-living but structurally robust materials to facilitate both immediate intraoperative stability by way of simple mechanics and long term stability by way of improved load transfer between the implant and the bone eliciting a beneficial biological response by the bone to said loading resulting in intimate and mechanically robust apposition between the composite interface and living tissue. It should be noted that such a method prevents excessive micromotion or strain at the interface between the implant (and/or the composite interface) and living tissue during the postoperative healing process, which, in essence, gives the bone a chance to further stabilize its fixation to the implant by way of bone modeling or remodeling in response to load transfer. Specifically, it is highly beneficial to maintain the strain state within living bone at and/or in the general vicinity of the bone implant interface within a range of 50 microstrain to 4000 microstrain so as to elicit the formation of bone tissue at and around the interface—strain levels in excess of 4000 microstrain or less than 50 microstrain are very likely to elicit the formation of fibrocartilagenous tissues at the interface which may lead to aseptic loosening of the implant. In the embodiment where the bone cement is injected, a small hole located at or beneath the skim cut allows for the injection of the material beneath the implant to achieve intimate and controlled interdigitation.

Figure 111:
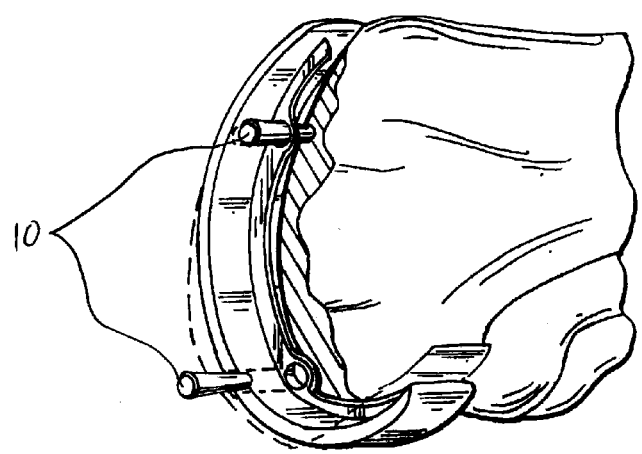

Alternatively, the implant could be seated 'over' the freshly cut concave surfaces, and a slurry of biologically active and/or mechanically robust material(s) injected into the gaps between the implant and the bone under controlled pressure. Injection could be achieved via the portal 12 shown in FIG. 34. Such a slurry may comprise a mixture of substances such as morselized patient bone and bone cement, but alternative or additional materials including bone substitutes, osteobiologicals such as bone morphogenic proteins, antibiotics, or even living cells such as T cells known to promote postoperative healing and long term implant fixation. Beneficially, a fin feature may be added to these embodiments to facilitate additional mechanical stability, and said stem feature could beneficially possess an aperture for cross-pin fixation as described below for use in conjunction with the cross pins 10 represented in FIG. 111.

Importantly, it is an objective of the embodiments of the present invention to preserve living, structurally viable bone tissue to facilitate the efficacy of any subsequent revision procedures. Further, the location and geometry of the concave tibial cut allows for the use of a bearing insert (conventionally made of materials such as polyethylene or other materials capable of 'whetting' or mimicking the benefits of 'whetting' during bearing contact; mimicking constituting, in one embodiment, the absence or mitigation of wear debris generation despite the application of significant bearing forces, in TKA in excess of 200 lbs and often as much as 500 lbs or more) whose 'underside' is convexly shaped to mate with a concavely shaped mating or accommodating surface in the upper surface of the tibial implant or 'baseplate' as it is sometimes referred to. This allows for a tibial insert(s) whose thickness, in the areas beneath where the femoral implant bears against the tibial insert, may be equal to or greater than those insert thicknesses used in the past (those associated with predominantly planar tibial cuts) while require removal of significantly less structurally viable bone from the cortical rim of the proximal tibia than past efforts. Determination of the geometry and location of the baseplate's concave surface and therefore the areas of greatest insert or bearing surface are easily determined by analysis of the wear patterns of retrieved tibial inserts. These embodiments of the present inventions also facilitate significant clinical benefits when applied to meniscal or rotating platform TKA designs as a high degree of conformity may be achieved while constraint is mitigated while preserving significantly more bone than prior art devices. Further, the reproducibility of the methods and apparatus described herein enable independent attachment of single compartment implants to bone to achieve Unicondylar, Bicondylar, Bicondylar and Patellofemoral, or Unicompartmental and Patellofemoral replacement of damaged bone surfaces while achieving the objectives of bone preservation, robust immediate and short and long term fixation, reproducibility of implant fixation and resulting location and orientation, and intraoperative ease of use.

It should be noted that the cutting profile of the cutting tool shown in FIG. 29 may be curved in manner beneficial to endplate preparation in intervertebral fusion, dynamic disc replacement, and/or nucleus replacement as the cutting profile closely approximately the natural geometry of the endplates and provides for intimate fit with such prostheses fixation surfaces. In adapting this embodiment to tibial resection in either partial or complete knee replacement, the cutting profile of the tool would be shaped as desired to create the aforementioned cut surfaces in either one continuous movement of a single cutting tool, or incremental use of one or more cutting tools to cut bone to the desired shape and in the appropriate location and orientation, in all degrees of freedom, with respect to the tibia and/or femur and/or patella and/or soft tissues of the knee joint.

Critically, in many applications of the tibial resection embodiments and methods described herein it is desirable that the Superior-Inferior thickness or diameter of the cutting tools used be less than the thickness of the bone to be removed in the creation of the cut surfaces so that the cutting surfaces of the cutting tool not contact soft tissue surface and bone surfaces located above the bone being removed. Alternatively, the cutting tool could be of such a thickness or diameter as to allow for the resection of both the femur and the tibia, or any such contiguous bones, to be prepared simultaneously with the passage of the cutting surfaces of a single tool across or along cut surfaces being created on both bones. Maintaining the desired geometric relationships between the contiguous or adjacent bone ends would be key in this embodiment of the present invention and could easily be obtained and maintained by use of a bracket fixed to the bones to establish and maintain the geometric relationship between said bones (see FIG. 30 for one embodiment of such a bracket employed to establish and maintain alignment between adjacent vertebral bodies.

FIGS. 35 through 40

FIGS. 35 through 40 show embodiments of the present invention for femoral resection. For the sake of clarity, it should be noted that any combination of the forms of the present invention disclosed herein may be modified or combined to form constructs not specifically disclosed herein, but still within the scope of the present invention. The embodiments represented in FIGS. 29 and 30 are outstanding examples of this, as one of ordinary skill in the art would clearly recognize the applicability and benefits of this embodiment for tibial and/or femoral resection in Unicondylar or Bicondylar procedures, for bone resection in ankle replacement or arthrodesis (fusion), mandibular advancement procedures, high tibial osteotomy procedures, proximal femoral and acetabular preparation in Hip Arthroplasty, and many other applications where reproducible and safe removal of living tissue during surgical intervention is beneficial.

Figure 40:
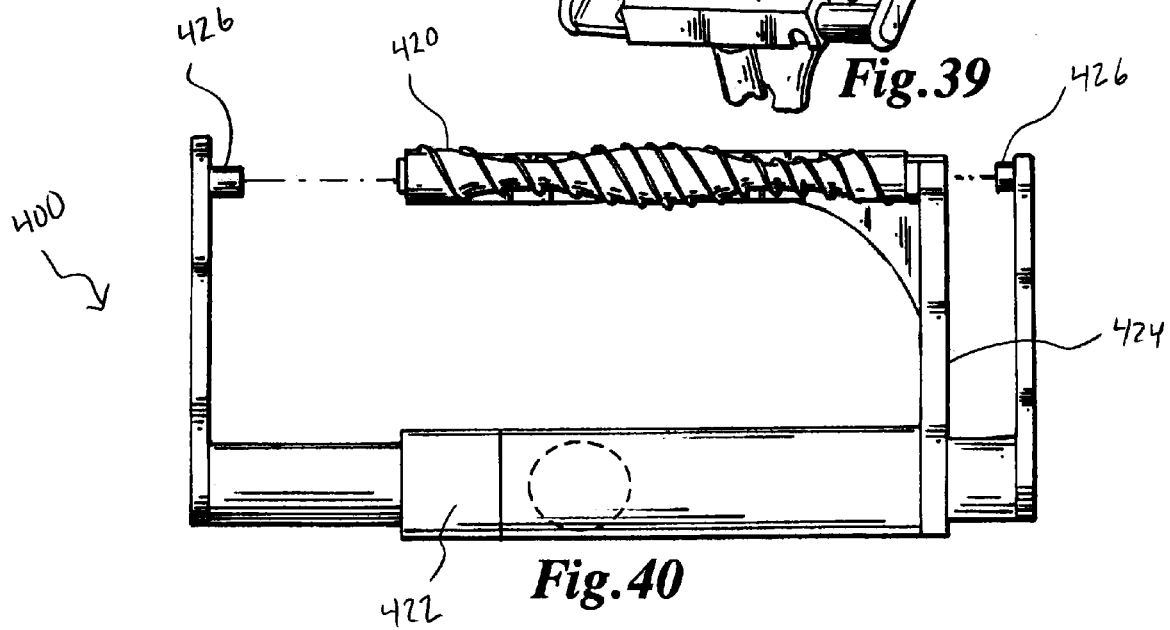
Figure 41:
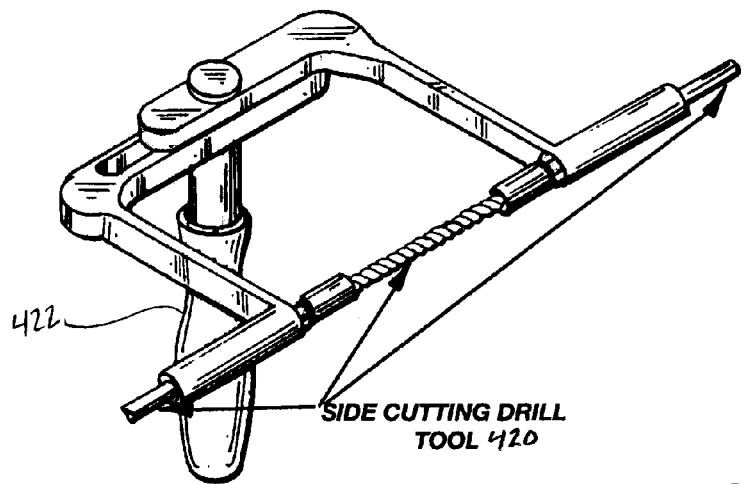
Figure 125:
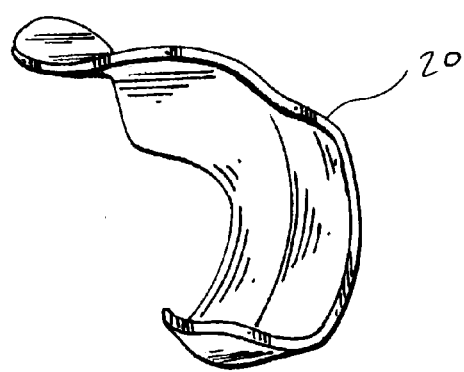
Figure 126:
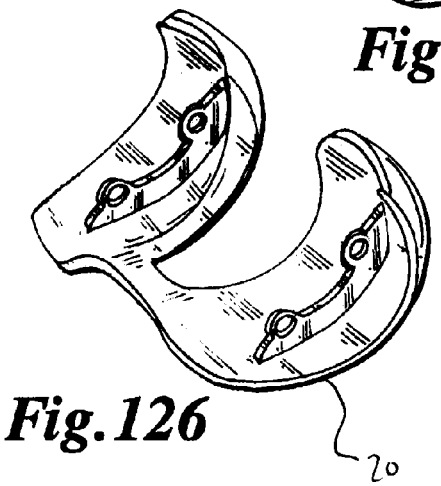
Figure 127:
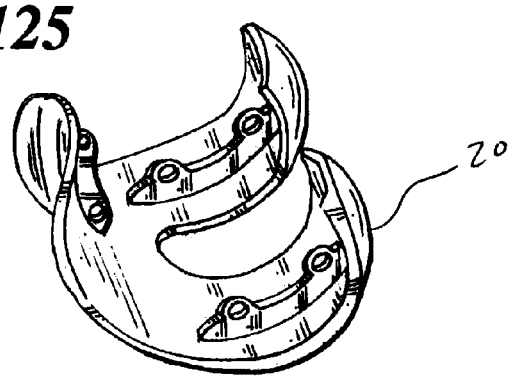

FIGS. 35-40 shows an embodiment 400 of the present invention wherein the guide plates 402 and guide surfaces 404 are located entirely outside the wound, but the side cutting drill 420 and handle 422 construct are not passed through mediolateral soft tissue portals described hereinabove. The side cutting drill controlling portion 424 of the handle is essentially 'snaked' into the less invasive wound/exposure/approach/incision and the guide engagement features 426 are engaged to the cutting guide at a location entirely outside the wound. As long as the axis of the engagement feature 426 is maintained as coaxial with the side cutting drill 420, the desired cut geometries will be attained despite manipulation of the handle 422 with respect to the guide 402. This method can be utilized to complete some or all of the desired cuts. Also, this embodiment of the current invention can be used to perform the posterior cut, posterior chamfer cut, and distal cut optionally using kinematic resection to reduce exposure requirements, and then removed from the wound and guide, flipped over 180 degrees from the orientation shown in FIG. 39, reinserted into the wound and into engagement with the guide 402 to cut the anterior chamfer cut and anterior cut with or without implementation of a kinematic resection technique and, optionally, with the knee in 15 degrees to 45 degrees to facilitate the soft tissue laxity and ease of use previously described. It should be noted that the mechanism for driving the side cutting drill 420 is not represented in these figures and that a number of different options may be used. One way to accomplish drive input is generically represented in FIG. 40, where a flexible drive shaft or bevel gear arrangement may be utilized to drive the side cutting form drill 420 shown. Alternatively, chain, belt, or pneumatic drive mechanisms may also be used. FIG. 40 also represents an embodiment of the present invention which allows for the accurate and precise preparation of curvilinear cut surfaces, beneficially used in conjunction with guides 403 containing curvilinear guide surfaces 405 as represented in FIGS. 61 and 62, to create cut surfaces for intimate attachment and fixation to implants 20 represented in FIGS. 125, 126, and/or 127.

Figure 94:
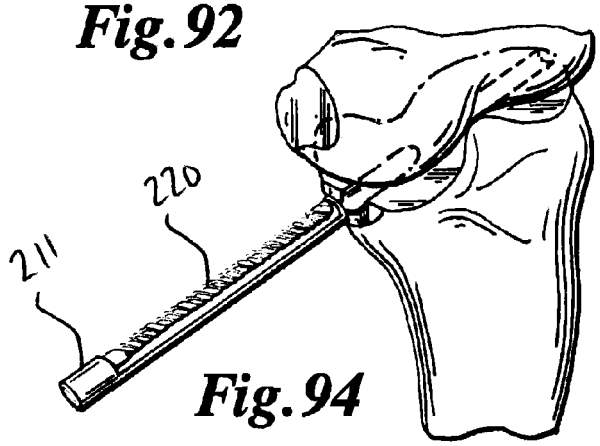
Figure 95:
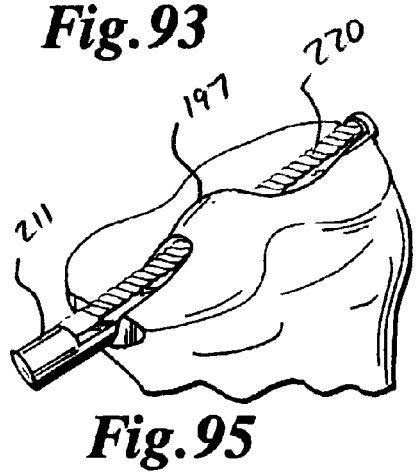
Figure 96:
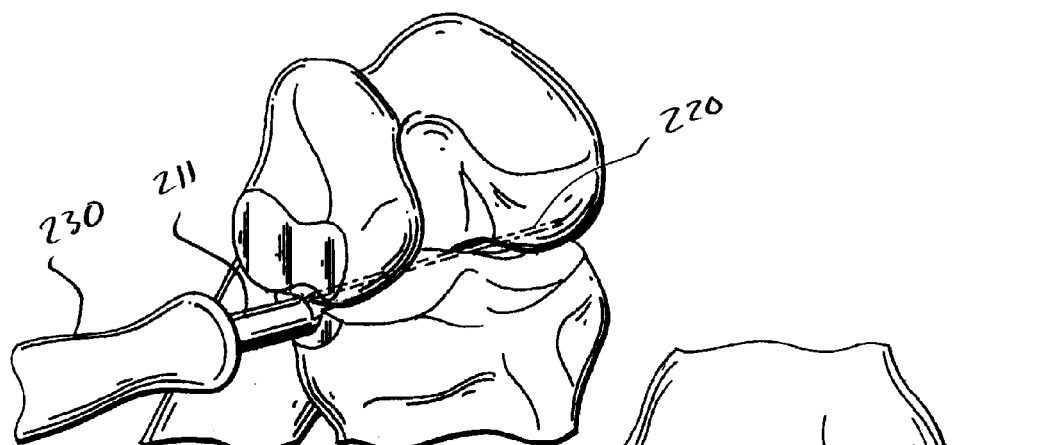
Figure 97:
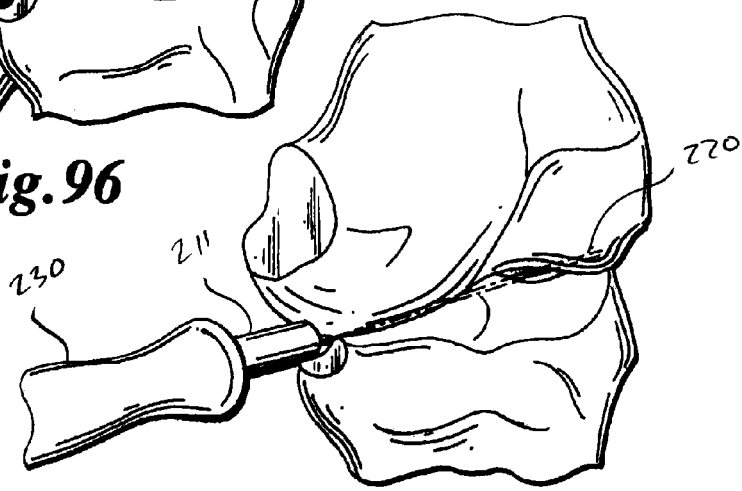
Figure 98:
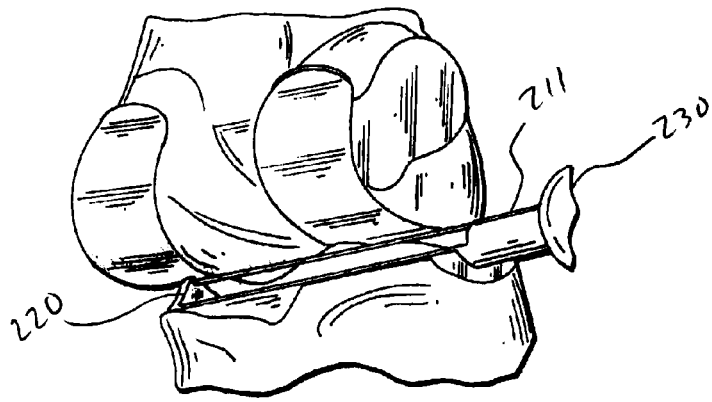
Figure 119:
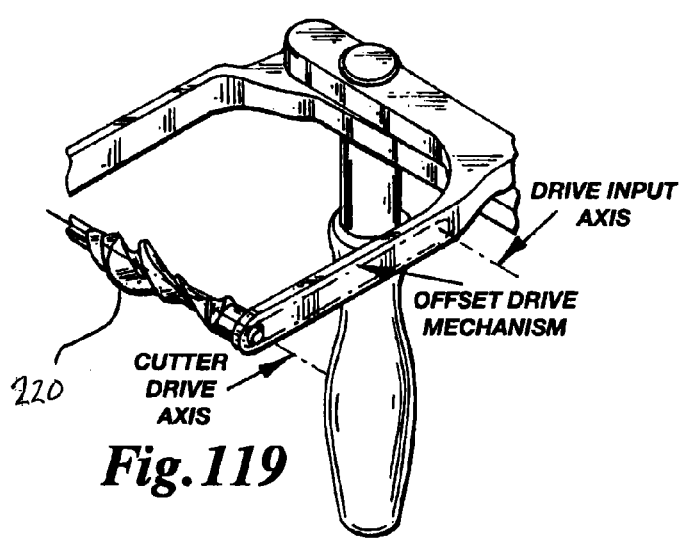

FIGS. 93 through 98 represent an implementation of the side cutting drill 220 embodiment of the present invention for cutting tools. It is of interest to note that the milling handle 211 shown could further be guided by the PBR guides of the present invention to further combine the accuracy and precision benefits of PBR with the soft tissue protection characteristics of tibially embedded femoral cutting tool. It should also be noted that the side cutting drill 220 with a curved cutting profile, similar to that shown in FIG. 119, could also be used to attain cut geometries possessing simultaneously curved or curvilinear cutting profiles and cutting paths. In utilizing such, it would be critical that the side to side location of the cutting profile of the cutting tool 220 be tightly controlled with respect to the desired side to side location of the implant as the side to side location of the implant would be dictated by the cut surfaces generated. Alternatively, a cutting tool with a linear cutting profile, as shown in FIG. 94, could be utilized to create cut surfaces with a linear cutting profile and a curved cutting path, and then a second cutter with a curved cutting profile could be used to create a second, contiguous or noncontiguous, cut with a curved cutting profile and/or path whose mediolateral location was closely controlled to result in proper fit and location of the prosthesis attached to said cut surfaces. It should be noted that the cutting path of the second cutter could be located within a single plane, such as for a bilateral femoral component design, or could be curvilinearly divergent from the plane containing the cutting path of the first cut surface. This would be useful for unilateral femoral component designs (ones which require separate left and right femoral implants) so as to allow for the implant design to reflect out of plane patellofemoral kinematics and/or out of plane tibiofemoral kinematics most accurately.

Interestingly, this embodiment of kinematic resection style resection could be modified to allow the cutting tool to be directly or indirectly linked to the movement of the patella with respect to the femur, or directly connected to the patella, to enable cutting of patellofemoral articular surfaces on the femur while moving the tibia and patella through ranges of motion about the tibia. The embodiments of cutting tools for use in attaining this include curvilinear end cutting mills or face cutters, side cutting drills with linear or non-linear cutting profiles, and other cutting tools capable of cutting the femur while engaged, directly or indirectly, to the patella. The side-to-side location of such cutters could be determined by engagement or adjustment with respect to a PBR or other guide, or simply by the natural kinematic path of the patella about the femur during flexion-extension of the knee joint.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A method for implanting an orthopedic prosthesis during knee arthroplasty surgery comprising:
   providing a cutting tool having a cutting profile defined along a longitudinal axis and presenting an effective width of the cutting profile transverse to the longitudinal axis and an effective length of the cutting profile along the longitudinal axis;
   creating a first opening in soft tissue proximate a bone on which a resected surface is to be created during the knee arthroplasty surgery, the first opening having a maximum dimension generally equal to or greater than the effective width of the cutting profile and less than the effective length of the cutting profile;
   inserting at least a portion of the cutting tool into the first opening such that the cutting profile is positioned to create the resected surface;
   creating at least a portion of the resected surface by relative movement of the cutting tool and the bone;
   creating a second opening in soft tissue proximate the bone; and
   inserting the orthopedic prosthesis to be attached to the resected surface through the second opening in soft tissue.

2. The method of claim 1, wherein the step of creating the maximum dimension of the first opening is created such that a ratio of the effective length of the cutting profile to the maximum dimension of the first opening is greater than 5:1.

3. The method of claim 1, wherein the bone to be resected is selected from the set of a femur and a tibia and the step of creating the first opening and inserting the cutting tool are performed such that the long axis of the cutting tool is initially oriented in a generally mediolateral orientation relative to the bone.

4. The method of claim 1, wherein the cutting tool further comprises at least one soft tissue protective sleeve surrounding the cutting profile proximate to a soft tissue region associated with the bone and wherein the at least one soft tissue protective sleeve is biased to track along a contour of a side of the bone and prevent the cutting profile from being exposed to the soft tissue region during the step of creating at least a portion of the resected surface.

5. The method of claim 1, wherein the step of creating the first opening comprises utilizing a pilot drill to create a bore in the bone to be resected and the cutting tool used in the step of inserting at least a portion of the cutting tool into the first opening is a tool other than the pilot drill.

6. The method of claim 5, wherein the pilot drill has an end cutting arrangement and a non-cutting removal surface that minimizes the tendency of the pilot drill bit to drift off-axis as the bore in the bone is created.

7. The method of claim 1, wherein the step of creating the first opening further comprises creating a third opening in soft tissue similar to the first opening in soft tissue on a side of the bone generally opposite to the first opening.

8. The method of claim 7, wherein the step of inserting at least a portion of the cutting tool into the first opening results in a portion of the cutting tool extending through the third opening.

9. The method of claim 8, wherein the wherein the cutting tool further comprises a pair of soft tissue protective sleeves, each soft tissue sleeve surrounding the cutting profile proximate a soft tissue region associated with the bone and proximate one of the first opening and the third opening, respectively, wherein the soft tissue protective sleeves are biased to track along a contour of a side of the bone and prevent the cutting profile from being exposed to the soft tissue region during the step of creating at least a portion of the resected surface.

10. The method of claim 1, wherein the wherein the cutting tool further comprises a handle having at least one guide engaging surface operably connected thereto, and wherein the handle is manipulated to cause the guide engaging surface to traverse a cutting path defined by a cutting guide during the step of creating at least a portion of the resected surface.

11. The method of claim 10, wherein the handle is manipulated to cause the guide engaging surface to traverse the cutting path defined by the cutting guide while the bone is swung through a range of motion during the step of creating at least a portion of the resected surface.

12. The method of claim 1, wherein step of creating the first opening creates the first opening such that the maximum dimension is less than 0.1875 inches.

13. A method for implanting an orthopedic prosthesis during knee arthroplasty surgery comprising:
   providing a cutting tool having a cutting profile defined along a longitudinal axis and presenting an effective width of the cutting profile transverse to the longitudinal axis and an effective length of the cutting profile along the longitudinal axis, the cutting tool including at least one soft tissue protective sleeve surrounding the cutting profile proximate to a soft tissue region associated with the bone;

creating a first opening in soft tissue proximate a bone on which a resected surface is to be created during the knee arthroplasty surgery, the first opening having a maximum dimension generally equal to or greater than the effective width of the cutting profile and less than the effective length of the cutting profile;

creating a second opening in soft tissue proximate the bone on a side of the bone generally opposite to the first opening;

inserting at least a portion of the cutting tool into the first opening such that the cutting profile is positioned to create the resected surface;

creating at least a portion of the resected surface by relative movement of the cutting tool and the bone such that the at least one soft tissue protective sleeve is biased to track along a contour of a side of the bone and prevent the cutting profile from being exposed to the soft tissue region as the resected surface is created; and attaching the orthopedic prosthesis to the resected surface.

14. The method of claim 13, wherein the step of creating the first opening comprises utilizing a pilot drill to create a bore in the bone to be resected and the cutting tool used in the step of inserting at least a portion of the cutting tool into the first opening is a tool other than the pilot drill.

15. The method of claim 14, wherein the pilot drill has an end cutting arrangement and a non-cutting removal surface that minimizes the tendency of the pilot drill bit to drift off-axis as the bore in the bone is created.

16. The method of claim 13, wherein the step of inserting at least a portion of the cutting tool into the first opening results in a portion of the cutting tool extending through the second opening.

17. The method of claim 16, wherein the wherein the cutting tool further comprises a pair of soft tissue protective sleeves, each soft tissue sleeve surrounding the cutting profile proximate a soft tissue region associated with the bone and proximate one of the first opening and the second opening, respectively, wherein the soft tissue protective sleeves are biased to track along a contour of a side of the bone during the step of creating at least a portion of the resected surface.

18. The method of claim 13, wherein the wherein the cutting tool further comprises a handle having at least one guide engaging surface operably connected thereto, and wherein the handle is manipulated to cause the guide engaging surface to traverse a cutting path defined by a cutting guide during the step of creating at least a portion of the resected surface.

19. The method of claim 18, wherein the handle is manipulated to cause the guide engaging surface to traverse the cutting path defined by the cutting guide while the bone is swung through a range of motion during the step of creating at least a portion of the resected surface.

* * * * *